US011384101B2

(12) United States Patent
Dubovoy et al.

(10) Patent No.: US 11,384,101 B2
(45) Date of Patent: *Jul. 12, 2022

(54) ORAL CARE COMPOSITIONS

(71) Applicant: Colgate-Palmolive Company, New York, NY (US)

(72) Inventors: Viktor Dubovoy, Cresskill, NJ (US); Long Pan, Somerset, NJ (US); Ravi Subramanyam, Belle Mead, NJ (US); Tatiana Brinzari, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/889,093

(22) Filed: Jun. 1, 2020

(65) Prior Publication Data

US 2020/0291047 A1 Sep. 17, 2020

Related U.S. Application Data

(62) Division of application No. 16/216,677, filed on Dec. 11, 2018, now Pat. No. 10,703,766.

(60) Provisional application No. 62/607,360, filed on Dec. 19, 2017.

(51) Int. Cl.
*C07F 3/06* (2006.01)
*C07F 7/22* (2006.01)
*A61K 8/49* (2006.01)
*A61K 8/46* (2006.01)
*A61K 8/27* (2006.01)
*A61K 8/19* (2006.01)
*A61Q 11/00* (2006.01)

(52) U.S. Cl.
CPC ............ *C07F 3/06* (2013.01); *A61K 8/19* (2013.01); *A61K 8/27* (2013.01); *A61K 8/463* (2013.01); *A61K 8/4926* (2013.01); *A61Q 11/00* (2013.01); *C07F 7/2208* (2013.01); *A61K 2800/524* (2013.01); *A61K 2800/58* (2013.01); *A61K 2800/74* (2013.01)

(58) Field of Classification Search
CPC . C07F 3/06; C07F 7/2208; A61K 8/19; A61K 8/27; A61K 8/463; A61K 8/4926; A61K 2800/524; A61K 2800/58; A61K 2800/74; A61Q 11/00

See application file for complete search history.

(56) References Cited

U.S. PATENT DOCUMENTS

| 4,146,607 | A | 3/1979 | Ritchey |
| 5,300,289 | A | 4/1994 | Garlich et al. |
| 5,320,829 | A | 6/1994 | Garlich et al. |
| 5,948,390 | A | 9/1999 | Nelson et al. |
| 8,178,483 | B2 | 5/2012 | Masters et al. |
| 9,044,466 | B2 | 6/2015 | Cohen et al. |
| 9,861,563 | B2 | 1/2018 | Kirkpatrick-Liverman et al. |
| 10,703,766 | B2 | 7/2020 | Dubovoy et al. |
| 2005/0048007 | A1 | 3/2005 | Ruggles |
| 2008/0175801 | A1* | 7/2008 | Ramji .................. A61Q 11/00 424/53 |

FOREIGN PATENT DOCUMENTS

| JP | H08-053313 | 2/1996 |
| KR | 20180056225 | 5/2018 |
| RO | 127465 | 6/2012 |
| WO | 2001/070183 | 9/2001 |
| WO | 2009/130608 | 10/2009 |
| WO | 2014/098827 | 6/2014 |

OTHER PUBLICATIONS

Scifinder Search_Apr. 26, 2021 (Year: 2021).*
Google Search_Apr. 26, 2021 (Year: 2021).*
SciFinder_search_C42CI4H76N2Sn_Oct. 22, 2021 (Year: 2021).*
SciFinder_search_C21CI3H38NSn_Oct. 22, 2021 (Year: 2021).*
International Search Report and the Written Opinion of the International Searching Authority issued in international application PCT/US2018/064985 dated Mar. 6, 2019.
JPH08-53313, Kanae Toryo KK, "Underwater Antifouling Agent", Feb. 27, 1996, English language machine translation of abstract, Espacenet, date obtained:Jul. 31, 2019, 1 page https://worldwide.espacenet.com/publicationDetails/biblio?CC=JP&NR=H0853313A&KC=A&FT=D&ND=3&date=19960227&DB=&locale=en_EP.
Machine English Translation of RO-127465-A2 from Espacenet. (Year: 2019).
Mikurube et al., "Isomerization-induced introduction of metal cations into polyoxomolybdate-surfactant hybrid crystals", Inorganic Chemistry Communications, 73:45-48 (2016).
Palermo et al., "First Report About the Use of Micellar Keggin Heteropolyacids as Catalysts in the Green Multicomponent Synthesis of Nifedipine Derivatives", Catalysis Letters, 146(9):1634-1647 (2016).
Spurny et al., "Fallung der anionischen Nitratkomplexe von Ce 4+ and Pu 4+ mit Cetylpyridiniumnitrat", Monatshefte fur Chemie, 118:789-791 (1987).
STIC Search for ZnCl2 cationic ligand complexes. (Year: 2019).
Vo et al., "Noncovalent supramolecular assembly of hexagonally ordered mesoscale Prussian blue analogue", Microporous and Mesoporous Materials, Elsevier, 163: 211-214 (2012).

(Continued)

*Primary Examiner* — Michael P Cohen

(57) ABSTRACT

Described herein are complexes comprising a cationic antibacterial agent and a metal salt; oral care compositions comprising same; along with methods of making and using these complexes and compositions.

7 Claims, 15 Drawing Sheets

(56) References Cited

OTHER PUBLICATIONS

Yu et al., "Oxidative Desulfurization of Diesel Using Organic Salt of Polyoxometalate as an Efficient and Recoverable Phase-transfer Catalyst", Chemistry Letters 43(6):834-836 (2014).

Neve et al, "Crystal architecture and mesophase structure of long-chain N-alkylpyridinium tetrachlorometallates", Inorganica Chimica Acta (2002), vol. 338, pp. 51-58.

* cited by examiner

ORAL CARE COMPOSITIONS

CROSS-REFERENCE TO RELATED APPLICATIONS

This application is a divisional of U.S. application Ser. No. 16/216,677 filed Dec. 11, 2018 which claims priority to U.S. Provisional Patent Application Ser. No. 62/607,360, filed on Dec. 19, 2017.

BACKGROUND

Antibacterial agents are commonly incorporated into oral care compositions to destroy or retard the growth of bacteria that may cause dental plaque, caries or dental decay, or bad breath.

Many antibacterial agents are cationic in order to interact with the negatively-charged microbial cell membranes. However, many oral care compositions also include anionic surfactants, such as sodium lauryl sulfate. Anionic surfactants are believed to deactivate cationic antibacterial molecules. Thus, it has been a challenge to formulate oral care compositions that contain both a cationic antibacterial agent and an anionic surfactant.

Accordingly, it would be commercially desirable to have oral care compositions wherein highly efficacious cationic antibacterial agents can be formulated with anionic surfactant systems without a meaningful loss in antibacterial efficacy. Implementations of the present invention are designed to meet this, and other, needs.

BRIEF SUMMARY

This summary is intended merely to introduce a simplified summary of some aspects of one or more implementations of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a complex comprising a cationic antibacterial agent and a metal salt.

The metal salt may be a soluble metal salt.

The metal salt may include a divalent metal.

The metal salt may be selected from a zinc salt and a stannous salt.

The cationic antibacterial agent may include cetylpyridinium chloride (CPC) and the complex is a cetylpyridinium complex.

The molar ratio of the metal salt to cationic antibacterial agent may be from about 0.5:1 to about 2:1.

The metal salt may be a zinc salt and the cationic antibacterial agent may be CPC.

The zinc salt may be selected from: zinc chloride, zinc sulfate, zinc nitrate, zinc bromide, and zinc citrate.

The complex may have a structural formula of $[(C_{21}H_{38}N)_2][ZnCl_4]$.

The metal salt may be a stannous salt and the cationic antibacterial agent may be CPC.

The complex may have a structural formula of $[C_{21}H_{38}N][SnCl_3]$.

The foregoing and/or other aspects and utilities embodied in the present disclosure may also be achieved by providing an oral care composition, including a complex including a cationic antibacterial agent and a metal salt; a surfactant; and a cosmetically acceptable carrier.

The metal salt may be a soluble metal salt, and may include a divalent metal.

The soluble metal salt may be selected from a zinc salt and a stannous salt.

The zinc salt may be selected from: zinc chloride, zinc sulfate, zinc nitrate, zinc bromide, and zinc citrate.

The cationic antibacterial agent may include cetylpyridinium chloride (CPC).

The molar ratio of the metal salt to cationic antibacterial agent may be from about 0.5:1 to about 2:1.

The metal salt may be a zinc salt and the cationic antibacterial agent may be CPC, and the zinc salt may include zinc chloride.

The complex may have a structural formula of $[(C_{21}H_{38}N)_2][ZnCl_4]$.

The metal salt may be a stannous salt and the cationic antibacterial agent may be CPC.

The complex may have a structural formula of $[C_{21}H_{38}N][SnCl_3]$.

The surfactant may be an anionic surfactant selected from: sodium lauryl sulfate, sodium lauryl ether sulfate, ammonium lauryl sulfate, ammonium lauryl ether sulfate, sodium cocoyl monoglyceride sulfonate, sodium lauryl sarcosinate, sodium lauryl isoethionate, sodium laureth carboxylate, sodium dodecyl benzenesulfonate; and combinations of two or more thereof.

The oral care composition may include from about 0.01 wt. % to about 1.0 wt. % of said complex.

The oral care composition may include from about 0.10 wt. % to about 0.75 wt. % of said complex.

The oral care composition may be a paste; a gel; a mouthwash or mouthrinse; and a prophy.

The oral care composition may further include an oral care ingredient selected from: a thickening agent; an abrasive; a film; a whitening agent; a flavorant; a colorant; a pH modifying agent; and a sensitivity reducing agent (e.g. a basic amino acid).

The foregoing and/or other aspects and utilities embodied in the present disclosure may also be achieved by providing a method of treating, inhibiting, preventing, or ameliorating a symptom associated with a disease or condition of the oral cavity in a subject in need thereof, including administering the complex or the oral care composition described above to an oral cavity surface of said subject.

The disease or condition of the oral cavity may be erosion; malodor; excessive plaque; gingivitis; biofilm build-up; tooth decay; caries; and dentinal hypersensitivity.

The foregoing and/or other aspects and utilities embodied in the present disclosure may also be achieved by using a complex or an oral care composition as described above for treating, inhibiting, preventing, or ameliorating a symptom associated with a disease or condition of the oral cavity in a subject in need thereof.

The disease or condition of the oral cavity may be erosion; malodor; excessive plaque; gingivitis; biofilm build-up; tooth decay; caries; and dentinal hypersensitivity.

BRIEF DESCRIPTION OF THE DRAWINGS

The accompanying drawings, which are incorporated in and constitute a part of this specification, illustrate implementations of the present teachings. These and/or other aspects and advantages of the disclosure will become apparent and more readily appreciated from the following description of the various implementations, taken in conjunction with the accompanying drawings of which.

Figure 1:
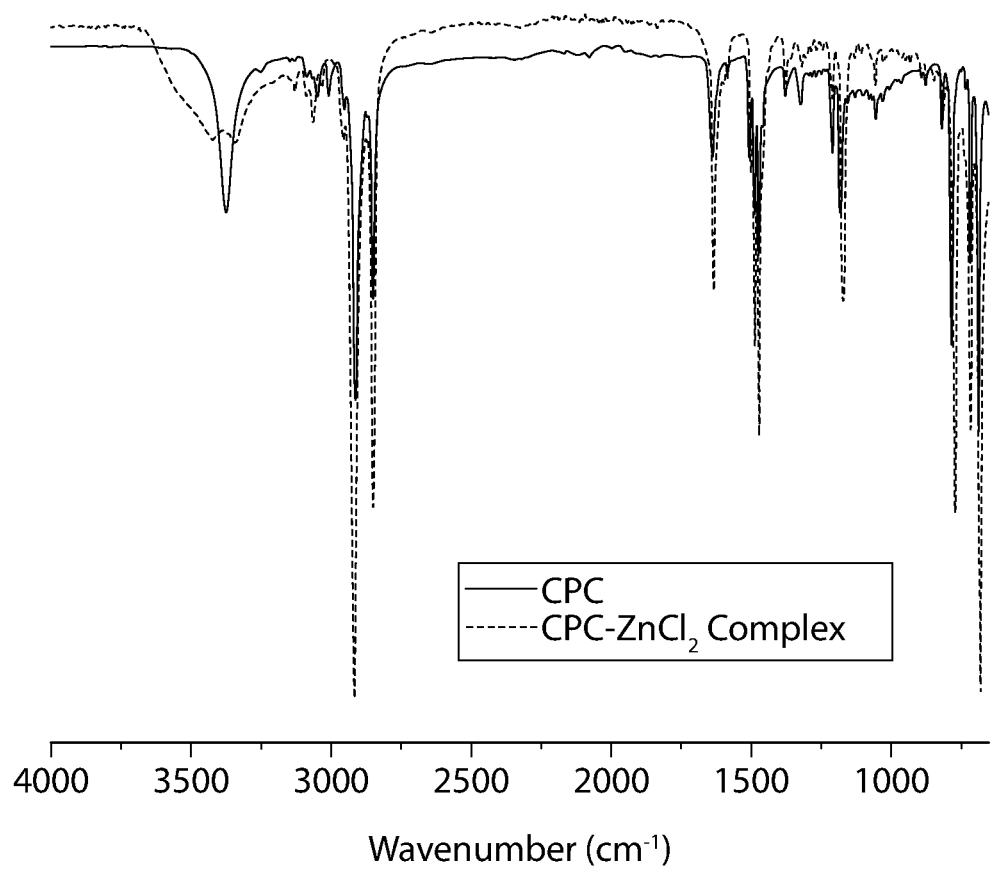
FIG. 1 illustrates the full spectrum (FTIR-ATR) infrared spectroscopy of samples of CPC-$ZnCl_2$ complex and CPC according to an implementation.

These drawings/figures are intended to be explanatory and not restrictive.

DETAILED DESCRIPTION

Reference will now be made in detail to the various implementations in the present disclosure, examples of which may be illustrated in any accompanying drawings and figures. The implementations are described below to provide a more complete understanding of the components, processes, compositions, and apparatuses disclosed herein. Any examples given are intended to be illustrative, and not restrictive. However, it will be apparent to one of ordinary skill in the art that the invention may be practiced without these specific details. In other instances, well-known methods, procedures, and components have not been described in detail so as not to unnecessarily obscure aspects of the implementations.

Throughout the specification and claims, the following terms take the meanings explicitly associated herein, unless the context clearly dictates otherwise. Phrases such as "in an implementation," "in certain implementations," and "in some implementations" as used herein do not necessarily refer to the same implementation(s), though they may. Furthermore, the phrases "in another implementation" and "in some other implementations" as used herein do not necessarily refer to a different implementation, although they may. As described below, various implementations may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes implementations containing A, B, or C, multiple examples of A, B, or C, or combinations of A/B, A/C, B/C, A/B/B/ B/B/C, A/B/C, etc. In addition, throughout the specification, the meaning of "a," "an," and "the" include plural references. The meaning of "in" includes "in" and "on."

All physical properties that are defined hereinafter are measured at 20° to 25° C. unless otherwise specified.

Unless otherwise specified, all percentages and amounts expressed herein and elsewhere in the specification should be understood to refer to percentages by weight. The amounts given are based on the active weight of the material.

Cetylpyridinium chloride (CPC) is a cationic antibacterial compound commonly used in mouthwashes, toothpastes, breath sprays, and other oral care compositions. CPC is soluble in alcohol and in aqueous solutions, and has a neutral pH. CPC acts as an antibacterial by binding and penetrating the negatively-charged surface of bacterial cell membranes to kill bacteria. However, the effectiveness of CPC as an antibacterial agent is reduced or inhibited in the presence of anionic surfactants, such as SLS. While not intending to be bound by any particular theory, it is believed that, when added to aqueous solutions, anionic surfactants ionize and have a negative charge. Accordingly, the negatively-charged anionic surfactant may bind to positively-charged cationic antibacterial molecules, such as CPC, and degrade their antibacterial activity. In other cases, anionic surfactants may cause cationic species to precipitate and thereby deactivate.

However, the inventors have unexpectedly and surprisingly created a new cationic antibacterial agent that is effective in oral care compositions including anionic surfactants. In particular, the inventors have created a cetylpyridinium complex which maintains effective antibacterial activity in the presence of anionic surfactants, such as SLS.

In certain implementations, the cetylpyridinium complex is a complex of cetylpyridinium chloride (CPC) and a soluble metal salt. The soluble metal salt may be selected from a zinc salt and a stannous salt. For example, the soluble salt may be one of zinc chloride, zinc sulfate, zinc nitrate, zinc bromide, and zinc citrate. In other implementations, the soluble salt may be stannous chloride. In other examples, other divalent (and monovalent) metals may also be used, such as calcium, copper, silver, zirconium, and aluminum In one implementation, the cetylpyridinium complex may be a complex of cetylpyridinium chloride (CPC) with zinc chloride ($ZnCl_2$). In other examples, the cetylpyridinium complex may be a complex of cetylpyridinium chloride (CPC) with stannous chloride ($SnCl_2$). Formula 1 illustrates the chemical structure of CPC and $ZnCl_2$. However, as described above, in other implementations, the cetylpyridinium complex may be a complex of cetylpyridinium bromide with zinc chloride ($ZnCl_2$) or zinc bromide ($ZnBr_2$), or a complex of cetylpyridinium chloride (CPC) with zinc bromide ($ZnBr_2$), or a complex of cetylpyridinium chloride (CPC) with stannous chloride ($SnCl_2$).

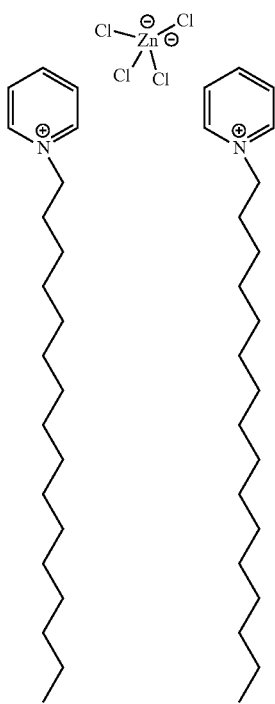

Formula 1

Accordingly, the cetylpyridinium complex may be, for example, a CPC-ZnCl$_2$ complex and/or a CPC-SnCl$_2$ complex, and an oral care composition includes an antibacterial agent, wherein the antibacterial agent comprises the cetylpyridinium complex. In other implementations, the antibacterial agent consists essentially of the cetylpyridinium complex, such as the CPC-ZnCl$_2$ complex. In certain implementations, the oral care composition lacks additional antibacterial agents. For example, the CPC-ZnCl$_2$ complex may be the only antibacterial agent in the oral care composition. In other implementations, the personal care composition may include additional antibacterial agents, such as zinc chloride or other metal salts.

The CPC-ZnCl$_2$ complex may be formed by the combination of CPC and ZnCl$_2$ aqueous solutions. For example, the CPC-ZnCl$_2$ complex may be a solid precipitate formed by the combination of CPC and ZnCl$_2$ aqueous solutions.

In one implementation, the CPC-ZnCl$_2$ complex was produced as follows: a 25 weight % CPC solution was created by dissolving 2.50 grams of anhydrous CPC in 10.01 grams of deionized water and a 75 weight % ZnCl$_2$ solution was created by dissolving 3.66 grams of anhydrous ZnCl$_2$ CPC in 4.90 grams of deionized water. 1.0 grams of the 75 weight % ZnCl$_2$ solution was then added dropwise to 3.76 grams of the 25 weight % CPC solution to obtain a Zn/CPC molar ratio of 2. The 75 weight % ZnCl$_2$ solution immediately precipitated upon contact with the 25 weight % CPC solution to produce the CPC-ZnCl$_2$ complex. In other implementations, the CPC-ZnCl$_2$ complex may be produced with other Zn/CPC molar ratios. For example, the amounts of CPC solution and ZnCl$_2$ solution, or the concentration of the CPC solution and ZnCl$_2$ solution, may be varied to obtain other molar ratios and the CPC-ZnCl$_2$ complex may be produced with a Zn/CPC molar ratio between 0.5 and 2.0. In one implementation, the CPC-ZnCl$_2$ complex may be produced with a Zn/CPC molar ratio of 0.5.

In another implementation, a larger amount of the CPC-ZnCl$_2$ complex was produced as follows: 5.0 grams of the 75% ZnCl$_2$ solution created as above was added dropwise to 18.75 grams of the 25 weight % CPC solution created as above to obtain a solid precipitate. The solid precipitate was then filtered and washed using 500 mL of deionized water followed by 5 mL of methanol and left in a 50° C. oven to dry overnight. The dried powder was chopped into a fine powder in a scintillation vial and left in a 50° C. oven for an hour under vacuum to produce the CPC-ZnCl$_2$ complex.

The CPC-ZnCl$_2$ complex was then mixed with deionized water to create 0.1, 0.5, 1.0, and 10.0 weight % CPC aqueous solutions to evaluated the solubility of the CPC-ZnCl$_2$ complex at both room temperature (23-24° C.) and at physiological temperature (36-37° C.). At room temperature, the 0.1 and 0.5 weight % solutions were soluble, while the 1.0 and 10.0 weight % solutions exhibited undissolved CPC-ZnCl$_2$ complex even after 24 hours of aging. Similarly, at physiological temperature, the 1.0 weight % solution was soluble, whereas the 10 weight % solution was not fully soluble. In contrast, CPC and ZnCl$_2$ are readily soluble in water. For example, ZnCl$_2$ was readily soluble in water at concentrations of up to 75 weight % at room temperature. Similarly, CPC was readily soluble in water at concentrations of up to 25 weight %, while producing a translucent gel or soft-solid material at concentrations greater than 40 weight % at room temperature.

Accordingly, in some implementations, the CPC-ZnCl$_2$ complex had at least a 25-fold reduction in solubility when compared to the CPC and ZnCl$_2$ reactants separately.

Similarly, CPC has a melting point of 77° C. In contrast, in some implementations, the CPC-ZnCl$_2$ complex transforms into a gel form at around 50° C. The reduction in solubility and changes in melting point are evidence that the CPC-ZnCl$_2$ complex is not a mere mixture of CPC and ZnCl$_2$, but involves a covalently or ionically-bound complex.

FIG. 1 illustrates the full spectrum (FTIR-ATR) infrared spectroscopy of samples of CPC-ZnCl$_2$ complex and CPC according to an implementation.

Figure 2:
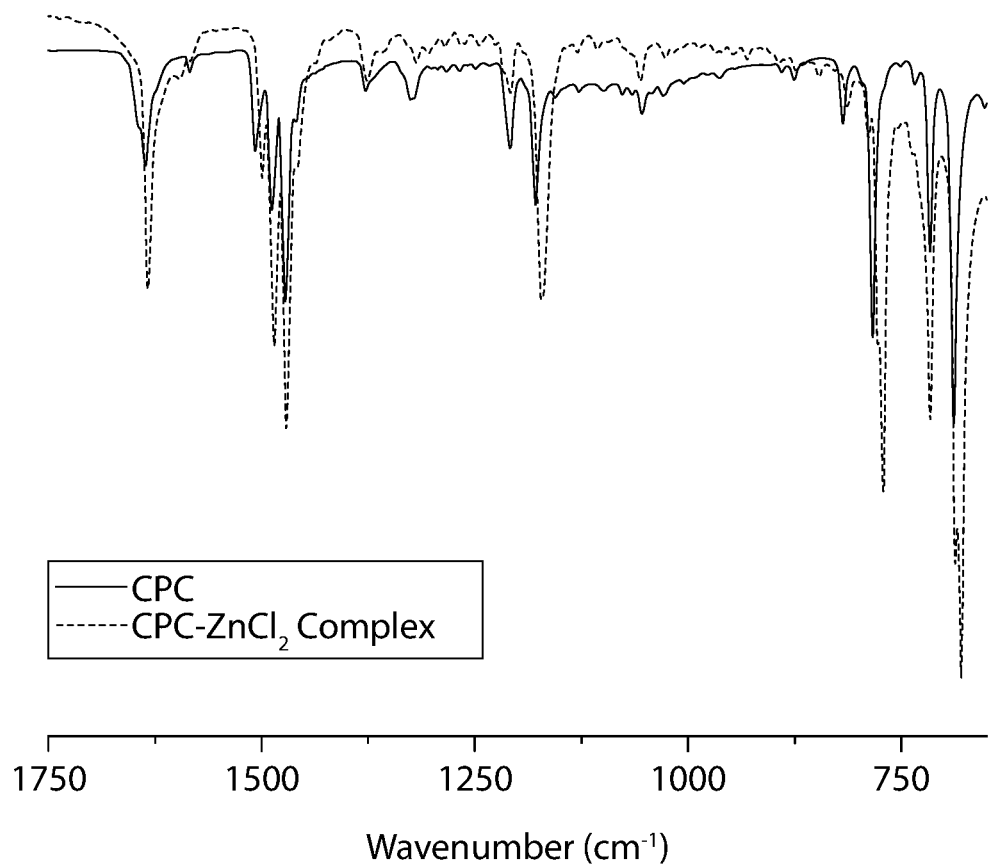
FIG. 2 illustrates the fingerprint region (FTIR-ATR) infrared spectroscopy of the CPC-$ZnCl_2$ complex and CPC samples of FIG. 1.

FIG. 2 illustrates the fingerprint region (FTIR-ATR) infrared spectroscopy of the CPC-ZnCl$_2$ complex and CPC samples of FIG. 1.

As illustrated in FIGS. 1 and 2, the most notable difference between the infrared spectroscopy for the CPC-ZnCl$_2$ complex and CPC is observed at the medium strength absorption band located around 3300 cm$^{-1}$, where after the addition of the ZnCl$_2$ and thermal treatment the CPC's band at 3300 cm$^{-1}$ splits into two (possible symmetric and asymmetric counterparts) distinct bands. That is, FIG. 1 illustrates significant changes in the Nitrogen vibrations (ca. 3500 cm$^{-1}$). This is more apparent in the fingerprint region illustrated in FIG. 2. The fingerprint region of FIG. 2 shows significant shifts/changes throughout the whole region which suggests structural differences of the CPC-ZnCl$_2$ complex and CPC samples further evidencing that the CPC-ZnCl$_2$ complex is not a mere mixture of CPC and ZnCl$_2$, but involves a covalently or ionically-bound complex.

A CPC-ZnCl$_2$ complex sample for elemental analysis was created by mixing 0.046 g of the CPC-ZnCl$_2$ complex as created above with 9.20 g of deionized water. The elemental analysis indicated 0.11 weight % Zn and 0.15 weight % Cl present in the solution. Accordingly, the elemental analysis suggests a Cl$^-$/Zn$^{2+}$ molar ratio of 2.5 which corresponds to the stoichiometry of 2 ZnCl$_2$:1 CPC, and is consistent with 2 ZnCl$_2$ molecules chelating a single Cl$^-$ from the CPC structure generating a [Zn$_2$Cl$_5$] moiety.

Accordingly, in certain implementations, the CPC-ZnCl$_2$ complex is a solid precipitate. The CPC-ZnCl$_2$ complex may also have a significantly reduced water solubility when compared to CPC.

To further elucidate the differences between the CPC-ZnCl$_2$ complex and CPC, samples of the CPC-ZnCl$_2$ complex prepared as described above were dissolved in solvent and re-crystallized to study implementations of its crystalline structure. In particular, crystals of the CPC-ZnCl$_2$ complex were made suitable for X-ray crystallography by dissolving samples of the CPC-ZnCl$_2$ complex (prepared as described above) in acetone and methanol, and re-crystallizing the CPC-ZnCl$_2$ complex by slow evaporation at room temperature. The X-ray diffraction data was collected using a Bruker D8 Venture PHOTON 100 CMOS system equipped with a Cu K$\alpha$ INCOATEC ImuS micro-focus source ($\lambda$=1.54178 Å). The X-ray diffraction data was collected at both 100 K and 298 K for the CPC-ZnCl$_2$ complex dissolved in methanol (Sample A) and at both 100 K and 273 K for the CPC-ZnCl$_2$ complex dissolved in acetone (Sample B). Indexing was performed using APEX3 (Difference Vectors method). Data integration and reduction were performed using SaintPlus 6.01. Absorption correction was performed by multi-scan method implemented in SADABS. Space group was determined using XPREP implemented in APEX3. The crystalline structure of the CPC-ZnCl$_2$ complex was solved using SHELXT (direct methods) and was refined using SHELXL-2017 (full-matrix least-squares on F$^2$) through OLEX2 interface program. All non-hydrogen atoms were refined anisotropically. Hydrogen atoms were placed in geometrically calculated positions and were included in the refinement process using riding model.

Figure 3:
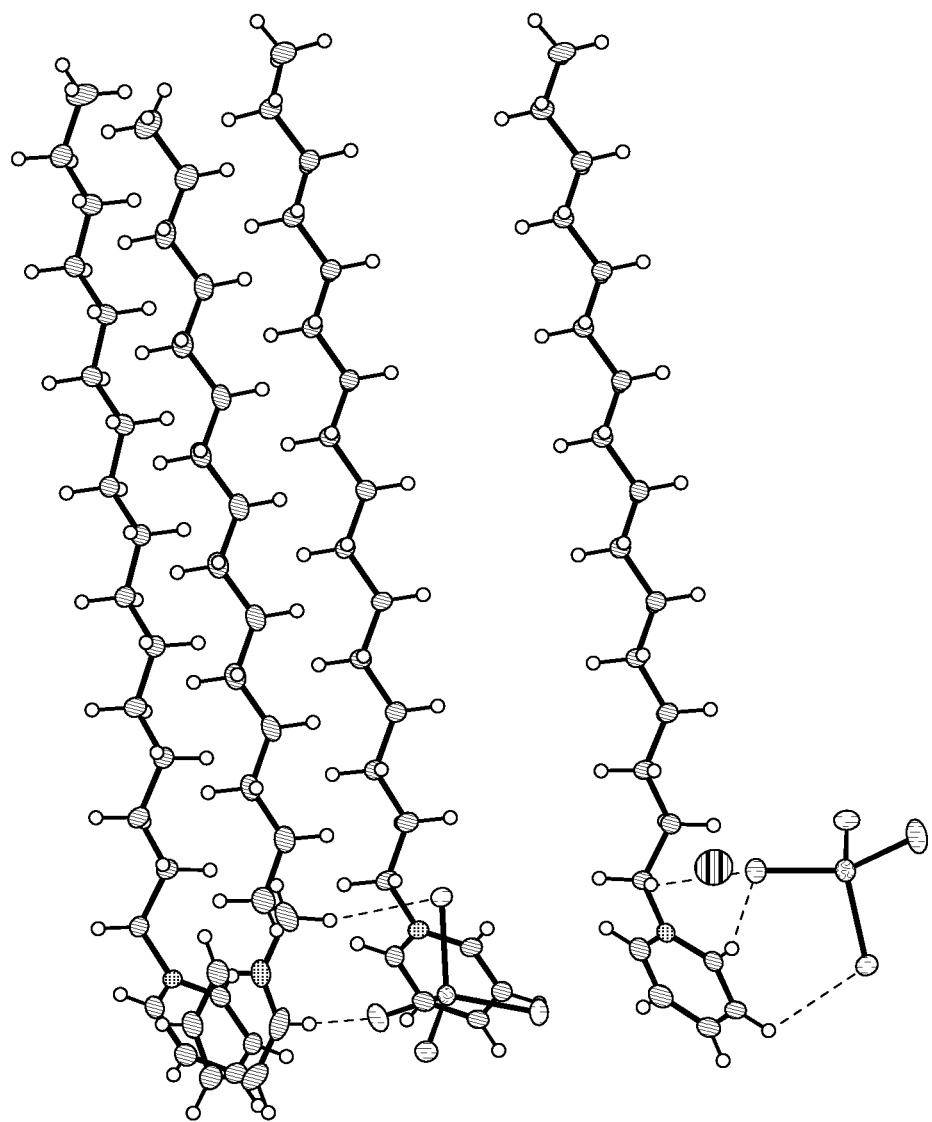
FIGS. 3-4 illustrate an X-ray diffraction (SCXRD) analysis of a CPC-$ZnCl_2$ complex according to an implementation.
Figure 4:
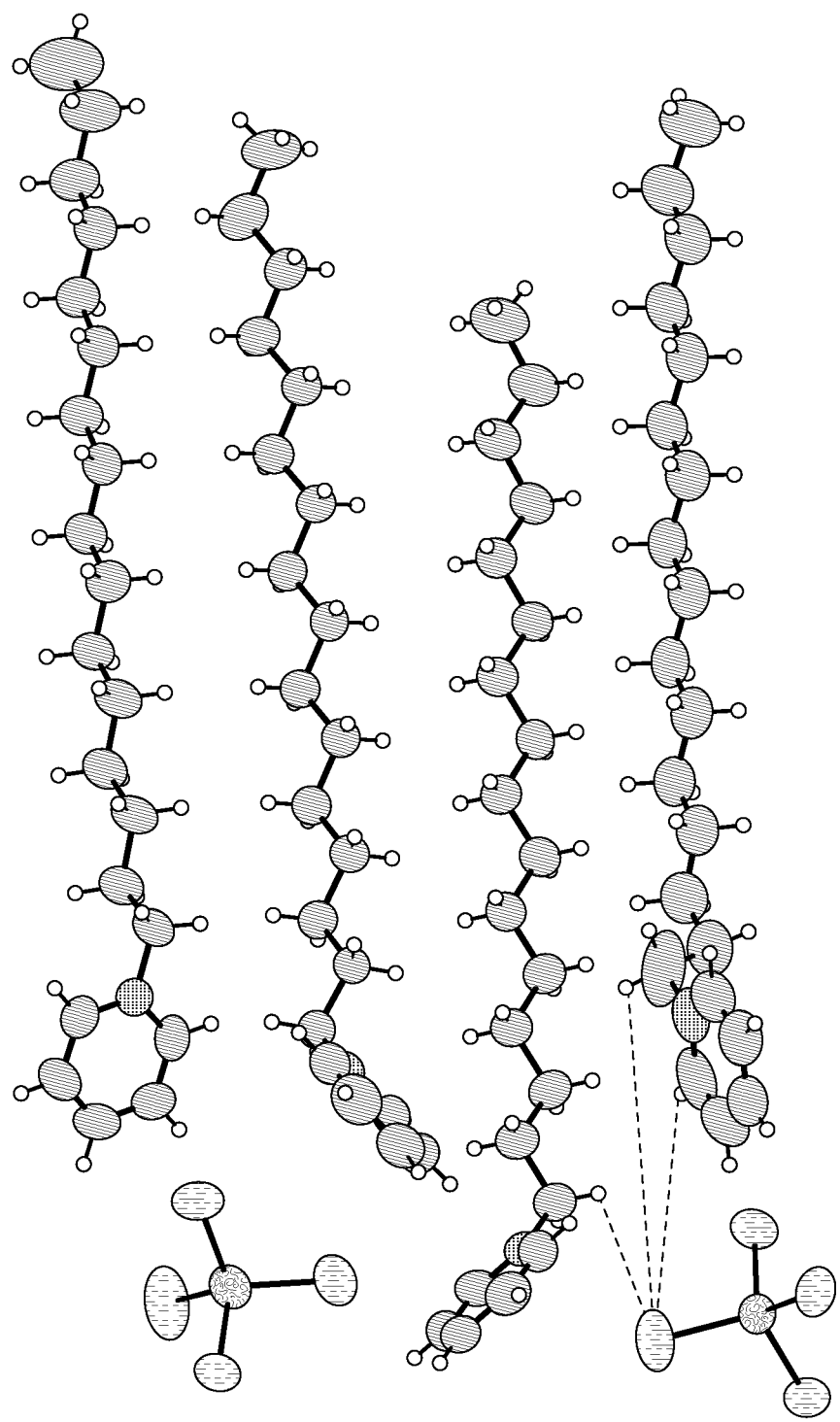

FIGS. 3-4 illustrate an X-ray diffraction (SCXRD) analysis of a CPC-ZnCl$_2$ complex according to an implementation. In particular, these figures illustrates a single crystal X-ray diffraction (SCXRD) analysis of Sample B at both 100 K (FIG. 3) and at 298 K (FIG. 4). As illustrated in FIGS. 3-4, the single crystal X-ray diffraction (SCXRD) analysis carried out both at 100 K and 298 K shows that the coordination complex crystallizes in orthorhombic Pbca space group. At 100 K (FIG. 3), the structural formula for the CPC-ZnCl$_2$ complex may be described as [(C$_{21}$H$_{38}$N)$_2$][ZnCl$_4$].O, where four independent cationic CPC units are present along with two anionic ZnCl$_4^{2-}$ units. The tetrahedral ZnCl$_4^{2-}$ anions are slightly distorted with the largest Cl-Zn-Cl angle being 113.40°. The average Zn-Cl bond distance is 2.27 Å which is in the range of the distances reported for the isolated ZnCl$_4^{2-}$ anions (2.26-2.29 Å) in the Cambridge Structural Database (CSD). The bond distances and angles for the organic cations also match quite well with those reported in the literature. The pyridinium heads are present close to the anions while the alkyl chains point in the opposite direction for the cation. Three of the CPC units have an eclipsed conformation while the other unit stacks slightly above the plane containing the three units. The as-synthesized crystals contain disordered solvent that was modeled as water molecule (atom O1). The unit cell parameters for Sample B were calculated as (a=14.08, b=20.51, c=62.56).

Figure 5:
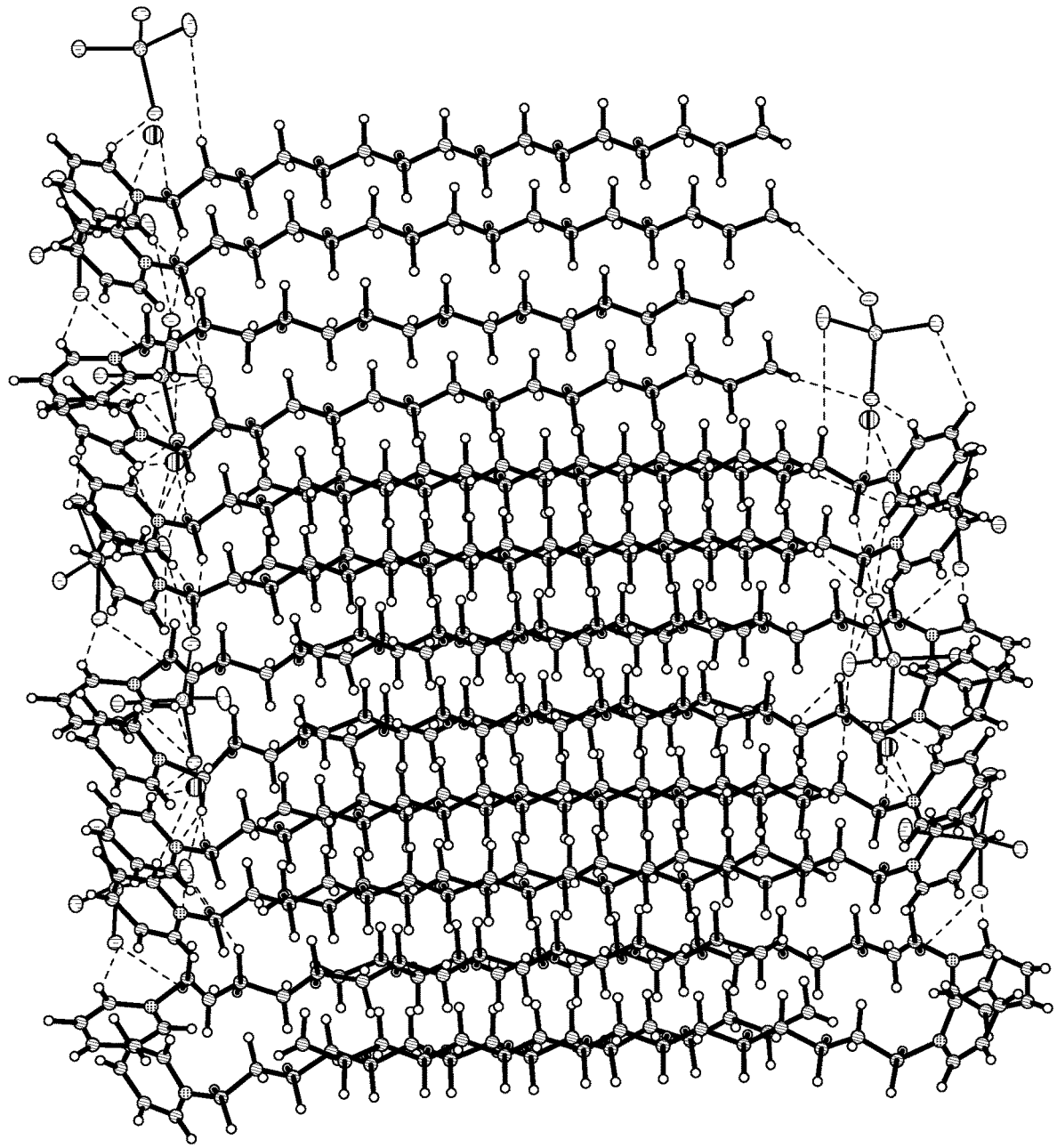
FIG. 5 illustrates packing of the structure illustrated in FIG. 3.

FIG. 5 illustrates packing of the structure illustrated in FIG. 3. As illustrated in FIG. 5, in some implementations, the packing arrangement of the CPC-ZnCl$_2$ complex analyzed at 100 K is similar to other reported [C16-Py]$_2$[MX$_4$] salts (M=Pd, Cd; X=Cl, Br) having a typical layer structure with alternating polar and apolar regions. A high degree of interdigitation is present within the apolar region.

The ionic layer is generated via repetition of superimposed rows of the pyridinium rings along the a axis. There are two different types of superimposed rows followed by superimposed rows of cations, which are again followed by two different superimposed rows of the pyridinium rings and different superimposed rows of cations. These are held together by C—H—Cl type secondary H-bonding interactions present between the chlorine atoms of the anion and the H atoms of the pyridinium ring and the alkyl chain (alpha and gamma H-atoms). The solvent oxygen atom also shows a weak interaction with the H-atom of the pyridinium ring. The H—Cl distances are in the range of the H-bonds with intermediate to weak strength and the number of C—H—Cl—M type interactions per ion pair and the distances are comparable to analogous Pd and Cd structures. The superimposed rows of pyridinium rings are interdigitated by the other superimposed rows of the next pyridinium ring and no significant $\pi$-$\pi$ interactions are observed.

Figure 6:
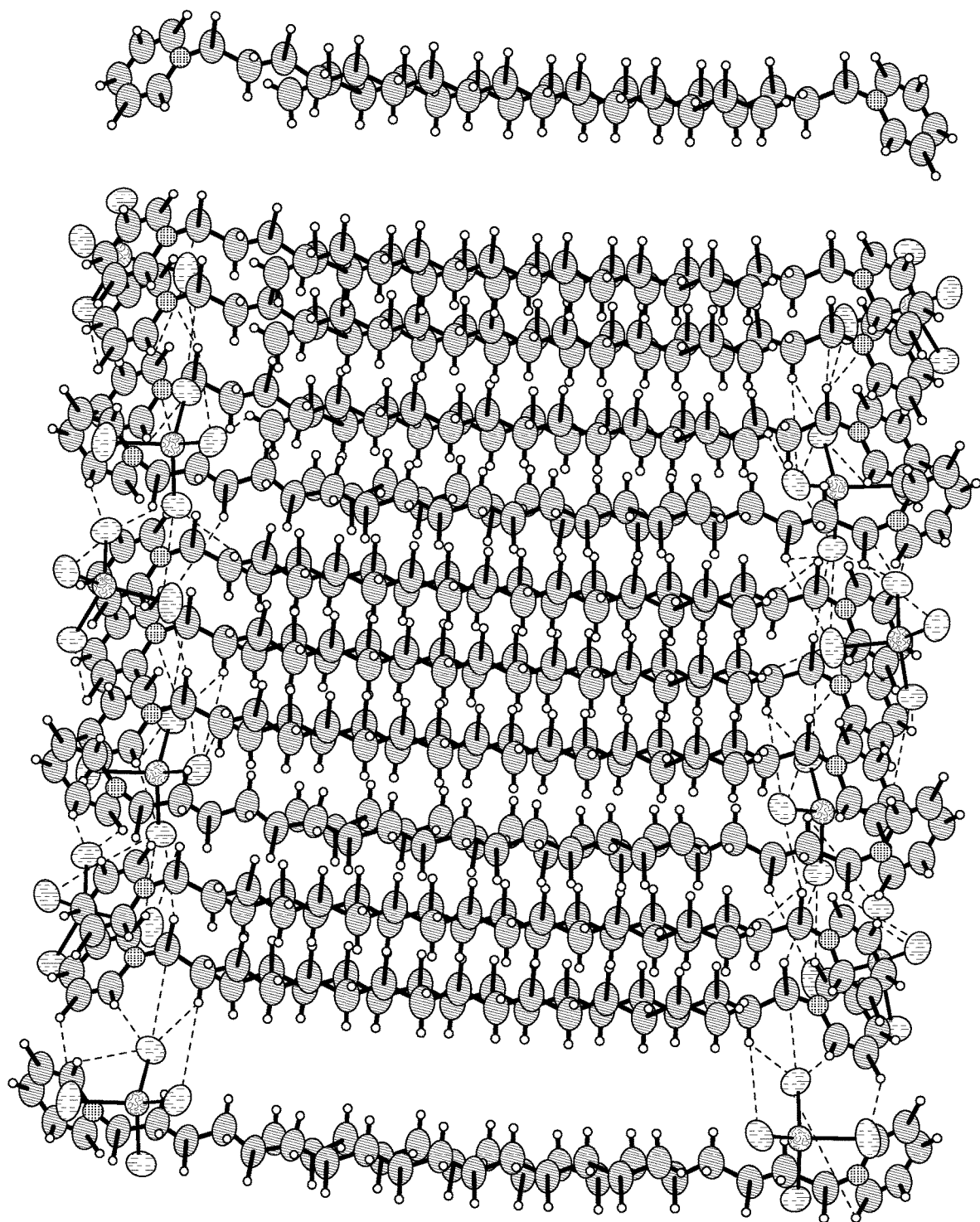
FIG. 6 illustrates packing of the structure illustrated in FIG. 4.

FIG. 6 illustrates packing of the structure illustrated in FIG. 4. As illustrated in FIG. 6, in some implementations, upon increasing the temperature to 298 K, the arrangement of the cationic and the anionic units relative to each other changes and the unit cell parameters change with the "a" unit cell parameter increasing significantly from 14.08 Å to 14.67 Å. At 298 K, the solvent molecule gets removed and the structural formula for the CPC-ZnCl$_2$ complex may be described as [(C$_{21}$H$_{38}$N)$_2$][ZnCl$_4$]. As illustrated in FIGS. 4 and 6, two of the CPC units are in an eclipsed conformation and the ZnCl$_4^{2-}$ anions are present between these units and another CPC unit. Another CPC unit lies underneath the eclipsed CPC units (FIG. 4).

As illustrated in FIG. 6, the packing behavior at 298 K is similar to the packing behavior at 100 K (FIG. 5), with layers being generated from the repetition of superimposed rows of the pyridinium rings along the a axis and the pairs of two types of superimposed rows of anions followed by superimposed rows of cations held together by the secondary C—H—Cl type hydrogen bonding interactions. The range of the H—Cl distances falls in the H-bonds with intermediate to weak strength and there are no significant $\pi$-$\pi$ interactions present. The distance between the zinc (II) centers (Zn01-Zn02) increases from 8.73 Å (at 100 K) to 9.05 Å (at 298 K).

Figure 7:
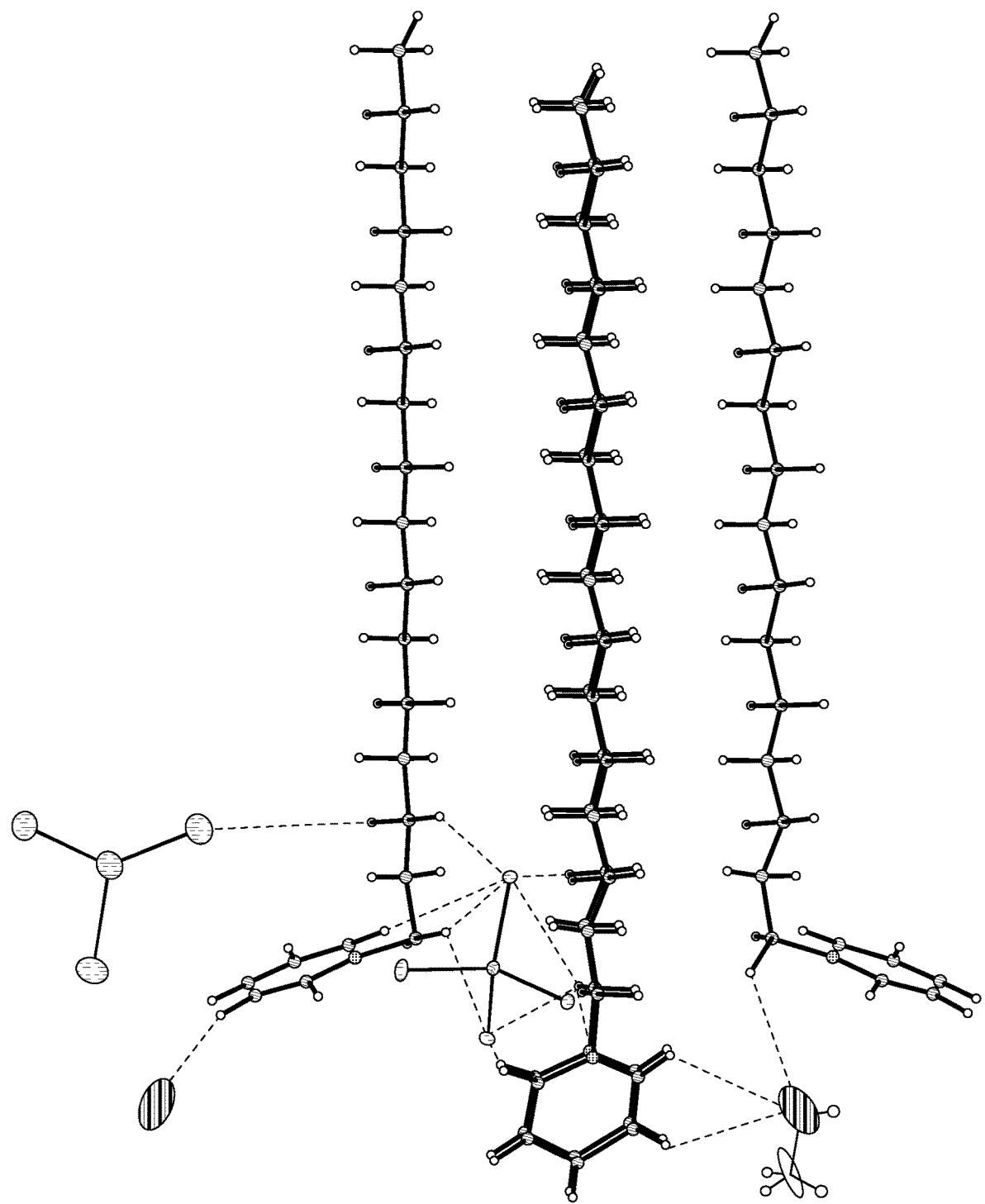
FIGS. 7-8 illustrate an X-ray diffraction (SCXRD) analysis of a CPC-$ZnCl_2$ complex according to an implementation.
Figure 8:
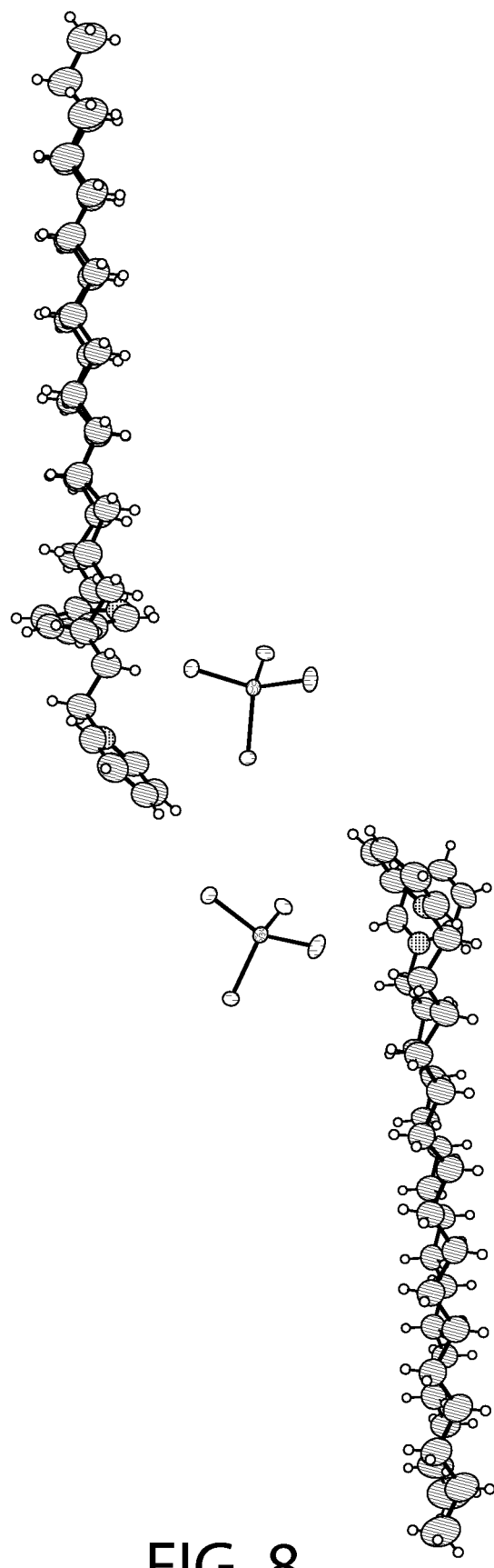

FIGS. 7-8 illustrates an X-ray diffraction (SCXRD) analysis of a CPC-ZnCl$_2$ complex according to an implementation. In particular, these figures illustrates a single crystal X-ray diffraction (SCXRD) analysis of Sample A at both 100 K (FIG. 7) and at 273 K (FIG. 8). As illustrated in FIGS. 7-8, the re-crystallization from methanol gave rise to a CPC-ZnCl$_2$ complex that may be described as [(C$_{21}$H$_{38}$N)$_2$][ZnCl$_4$].O.(CH$_3$OH). In certain implementations, this structure has the similar four independent cationic CPC units and the two anionic ZnCl$_4^{2-}$ units, but may display a different unit cell and packing of the structure. For example, the SCXRD analysis carried out at both 100 K (FIGS. 7) and 273 K (FIG. 8) revealed that Sample A crystallizes in the monoclinic P2(1)/c space group. The unit cell parameters (a=33.26, b=9.06, c=32.05) for Sample A at 100 K may be different from Sample B (a=14.08, b=20.51, c=62.56). As illustrated in FIGS. 7-8, there may be an elongation along the a axis and a decrease along the b and the c axis. In the asymmetric unit, two of the CPC units are eclipsed onto each other with one anionic ZnCl$_4^{2-}$ unit present between the two eclipsed CPC units and another CPC unit. Another CPC unit is stacked above the eclipsed CPC units. The structure contains disordered solvent which was modeled as water molecule (atom O1). Another solvent molecule is present that was modeled as methanol. The structural formula can be described as $[(C_{21}H_{38}N)_2][ZnCl_4].O.(CH_3OH)$.

As illustrated in FIGS. 7-8, the tetrahedral $ZnCl_4^{2-}$ anions are slightly distorted. One of the anionic unit has a significant distortion with the Cl—Zn—Cl angle being 119.50° due to disorder in the Cl atom. The average Zn—Cl bond distance (2.27 Å) lies in the 2.26-2.29 Å range of the distances reported for the isolated $ZnCl_4^{2-}$ anions in the Cambridge Structural Database (CSD).

Figure 9:
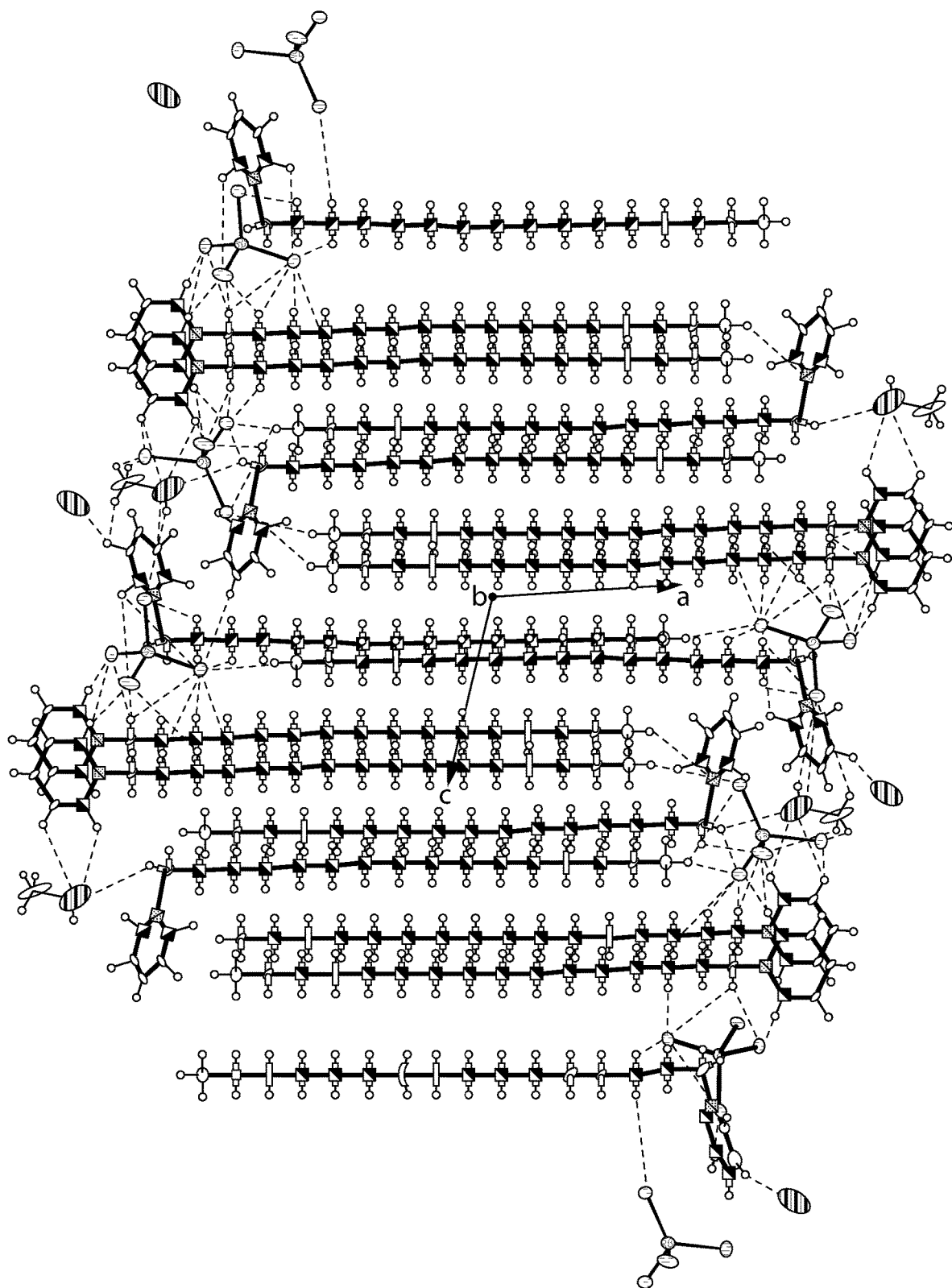
FIG. 9 illustrates packing of the structure illustrated in FIG. 7.

FIG. 9 illustrates packing of the structure illustrated in FIG. 7. As illustrated in FIG. 9, in some implementations, the packing arrangement of the CPC-$ZnCl_2$ complex analyzed at 100 K is similar to that of Sample B (layer structure with alternating polar and apolar regions) illustrated in FIG. 5. There is a high degree of interdigitation and the layer is generated via repetition of superimposed rows of the pyridinium rings along the b axis. There are two different types of superimposed rows of cations followed by the two different superimposed rows of anions. The supramolecular arrangement is attained via the secondary hydrogen bonding interactions of the C—H—Cl type and between the solvent oxygen and pyridinium hydrogen atoms. No significant π-π interactions are present.

Figure 10:
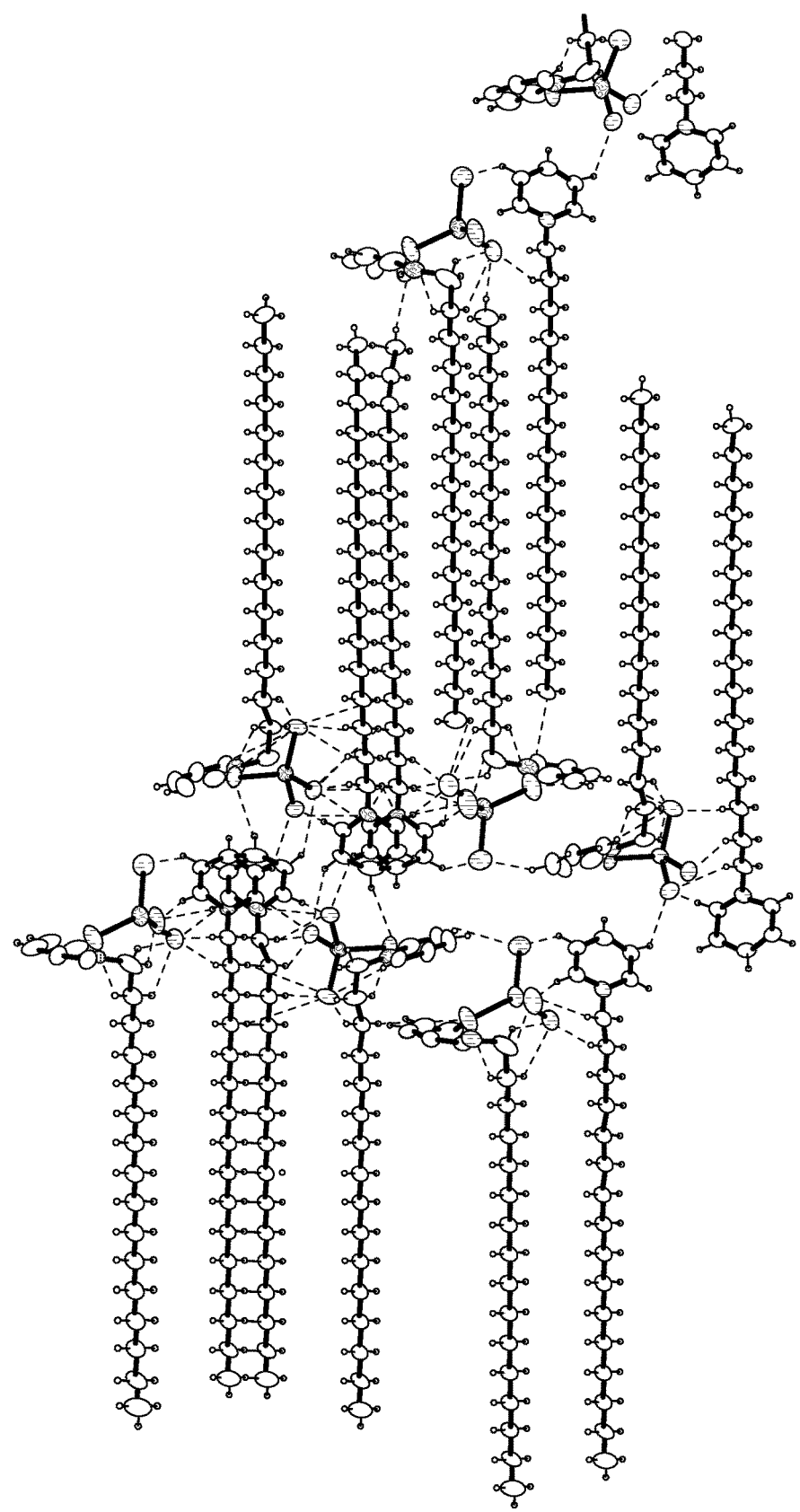
FIG. 10 illustrates packing of the structure illustrated in FIG. 8.

FIG. 10 illustrates packing of the structure illustrated in FIG. 8. As illustrated in FIG. 10, in some implementations, upon increasing the temperature to 273 K, structure adopts a different conformation with the two $ZnCl_4^{2-}$ anions present between the two pairs of two eclipsed CPC units. The unit cell parameters are also different from the 100 K structure with the c parameter increasing significantly from 32.05 Å to 32.98 Å. The distance between the zinc (II) centers (Zn01-Zn02) decreases from 8.94 Å (at 100 K) to 8.71 Å (at 273 K). The packing is similar having the layer structure with alternating polar and apolar regions with a high degree of interdigitation. The secondary hydrogen bonding interactions of the C—H—Cl type are stronger compared to the above structures but no significant π-π interaction is there.

Figure 11:
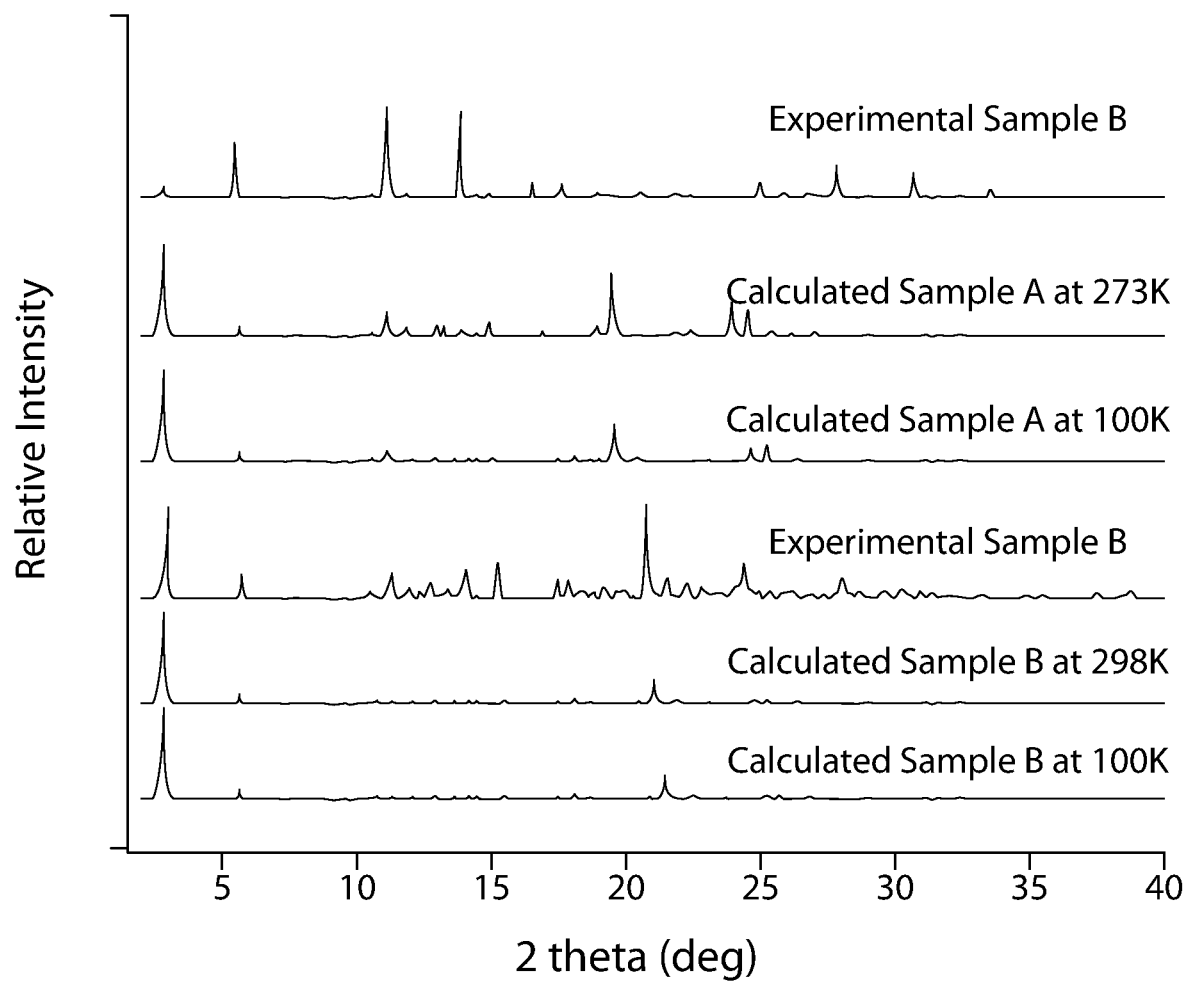
FIG. 11 illustrates a powder X-ray diffraction (PXRD) analysis of CPC-$ZnCl_2$ complex samples according to various implementations.

FIG. 11 illustrates a powder X-ray diffraction (PXRD) analysis of CPC-$ZnCl_2$ complex samples according to implementations. As illustrated in FIG. 11, powder X-ray diffraction (PXRD) analysis of the re-crystallized CPC-$ZnCl_2$ complex samples (Samples A and B) showed that it is in good agreement with the calculated structures at both 100 K and 298 K, confirming phase purity.

Accordingly, as illustrated in FIGS. 3-11, in some implementations, the CPC-$ZnCl_2$ complex can be described as having a $[(C_{21}H_{38}N)_2][ZnCl_4]$ structural formula. In addition, the crystallization analysis described above further evidence that the CPC-$ZnCl_2$ complex is not a mere mixture of CPC and $ZnCl_2$, but involves a covalently or ionically-bound complex.

In other implementations, the cetylpyridinium complex may be a complex of cetylpyridinium chloride (CPC) with a stannous chloride ($SnCl_2$).

The CPC-$SnCl_2$ complex may be formed by the combination of CPC and $SnCl_2$ aqueous solutions. For example, the CPC-$SnCl_2$ complex may be a solid precipitate formed by the combination of CPC and $ZnCl_2$ aqueous solutions. In one implementations, the CPC-$SnCl_2$ complex was formed as follows: a 10 weight % and a 25 weight % solutions was prepared using stannous chloride dihydrate ($SnCl_2.2H_2O$) and cetylpyridinium chloride monohydrate (CPC.$H_2O$), respectively, in absolute ethanol. The solutions were then sonicated to ensure complete dissolution. The stannous chloride solution was then added dropwise to the CPC solution. A crystalline "snow-flake" type material was then formed after several minutes. This material was filtered, washed with copious amounts of water, and characterized via ATR-FTIR and SCXRD to illustrate its nature as a CPC-$SnCl_2$ complex.

Figure 12:
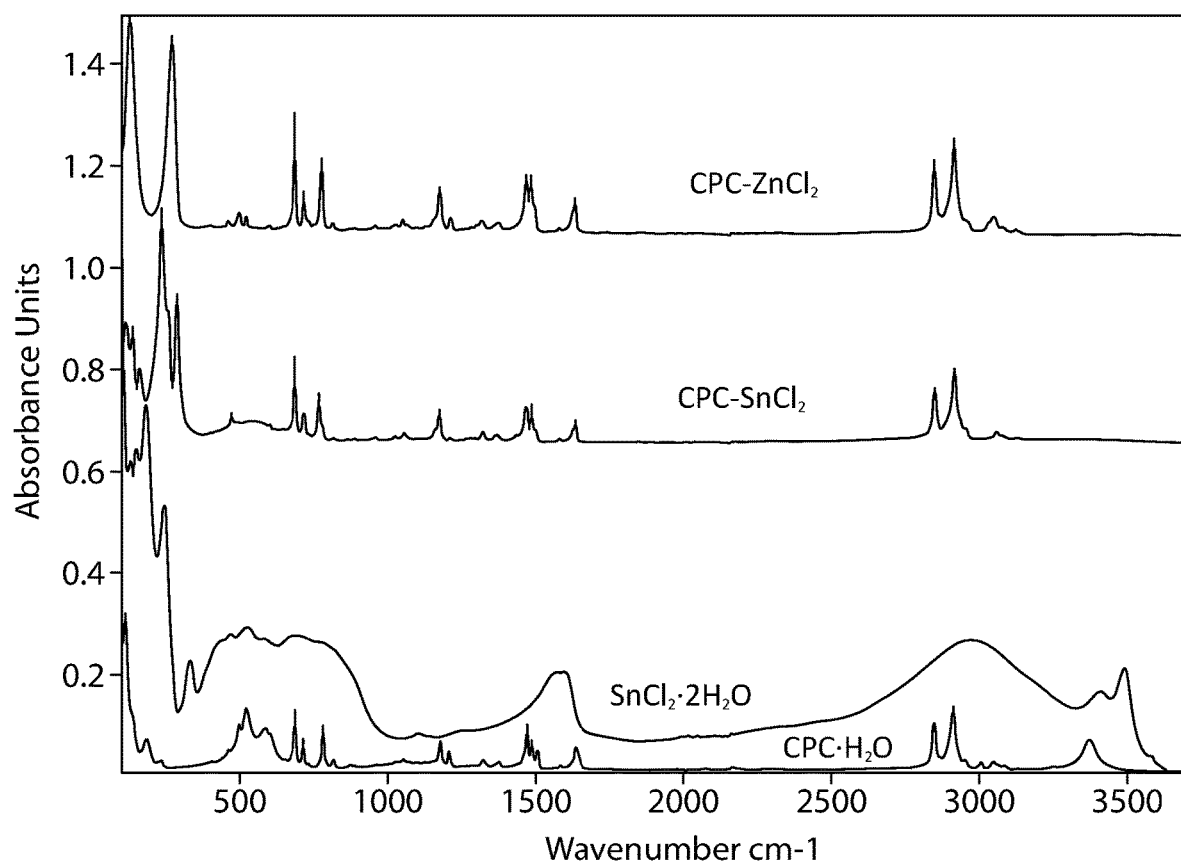
FIG. 12 illustrates a full spectrum (FTIR-ATR) infrared spectroscopy for samples of CPC-$ZnCl_2$ complex, CPC-$SnCl_2$ complex, $SnCl_2 \cdot 2H_2O$, and $CPC.H_2O$ according to an implementation.
Figure 13:
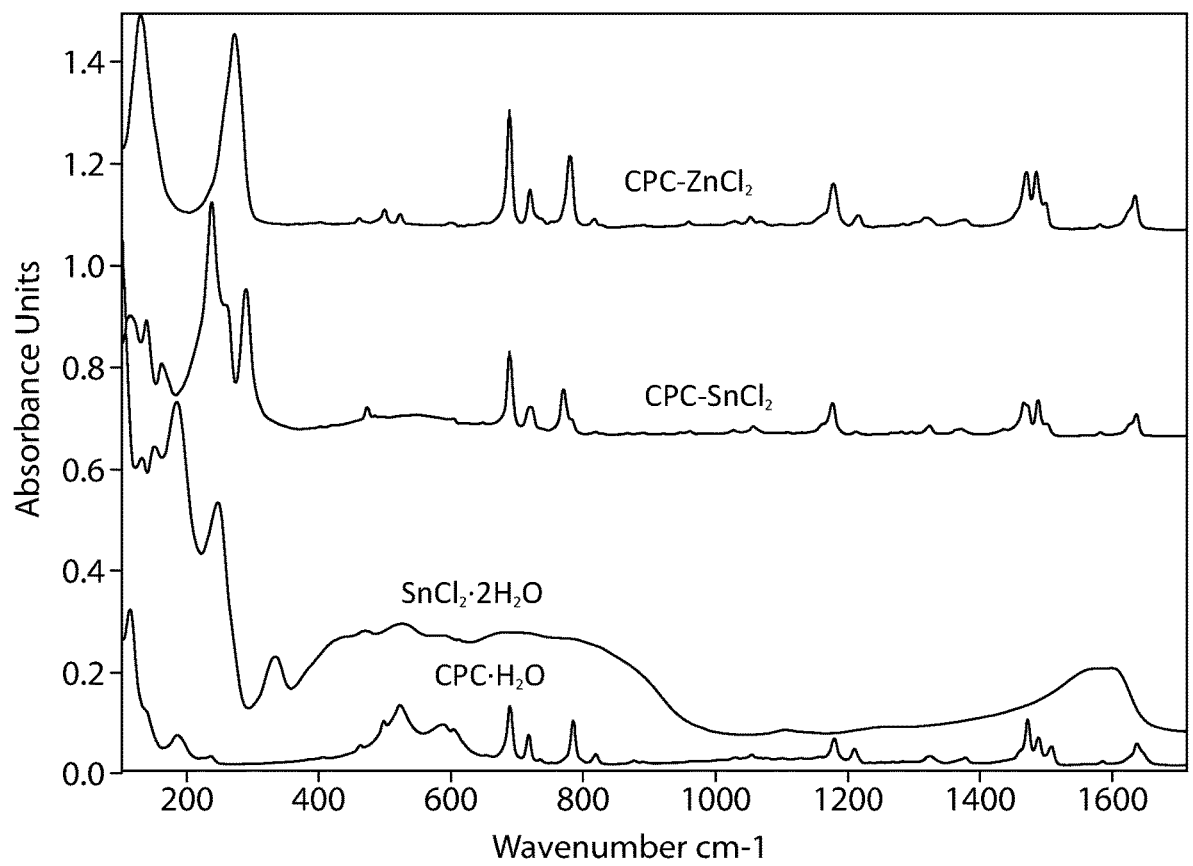
FIG. 13 illustrates a close-up view of the FTIR-ATR infrared spectroscopy of FIG. 12 in the 100-1700 cm-1 range.

FIG. 12 illustrates the full spectrum (FTIR-ATR) infrared spectroscopy of samples of CPC-$ZnCl_2$ complex, CPC-$SnCl_2$ complex, $SnCl_2.2H_2O$, and CPC.$H_2O$ according to an implementation. FIG. 13 illustrates a close-up view of the FTIR-ATR infrared spectroscopy of FIG. 12 in the 100-1700 cm-1 range. The Infrared spectra was collected using a Bruker Vertex 70 FTIR spectrometer (Bruker Optics, Billerica, MA) equipped with a GladiATR diamond ATR accessory (Pike technologies, Madison, Wis.). The spectral range was 80-4000 $cm^{-1}$ and a resolution of 4 $cm^{-1}$ was used. All measurements were carried out at room temperature.

As illustrated in FIGS. 12-13, the spectrum of the CPC-$SnCl_2$ complex sample clearly shows the fingerprint of the cetylpyridinium, confirming its presence in the sample. However, a close inspection of the spectrum also demonstrates that the bands of cetylpyridinium in the CPC-$SnCl_2$ complex sample do not match the pure CPC.$H_2O$ starting material: a majority of the bands related to $CH_2$, C=C, C=N and C—H stretching and bending vibrations of cetylpyridinium display shifted peak positions compared to the CPC.$H_2O$ starting material. The ν(OH) band near 3370 $cm^{-1}$ seen in CPC.$H_2O$ starting material has also disappeared in presence of Sn. Furthermore, a new cluster of bands below 340 $cm^{-1}$ (e.g., strong bands at 289, 260 and 237 $cm^{-1}$) is evident in the CPC-$SnCl_2$ complex sample, likely originating from the Sn-related vibrations. Comparison to the $SnCl_2.2H_2O$ starting material spectrum does not reveal presence of residual $SnCl_2.2H_2O$ starting material in the CPC-$SnCl_2$ complex sample. In addition, it is noteworthy that the spectra of the CPC-$SnCl_2$ complex sample and the CPC-$ZnCl_2$ complex sample are overall similar in the behavior of the cetylpyridinium vibrational bands in presence of metal. Accordingly, the FTIR data of FIGS. 12-13 evidence that the CPC-$SnCl_2$ complex is not merely a mixture of CPC and $SnCl_2$, but the formation of a new cetylpyridinium complex.

Figure 14:
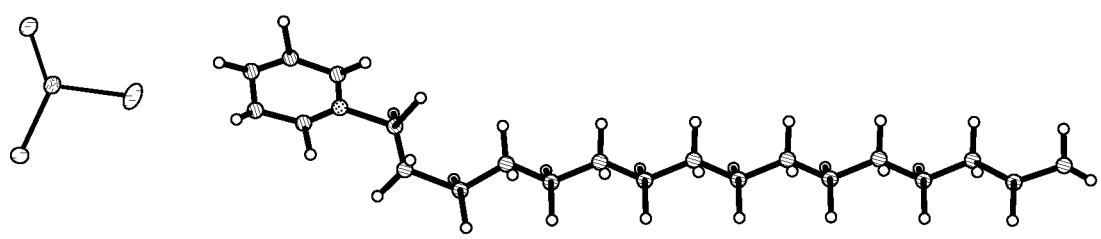
FIG. 14 illustrates an X-ray diffraction (SCXRD) analysis of a CPC-$SnCl_2$ complex according to an implementation.
Figure 15:
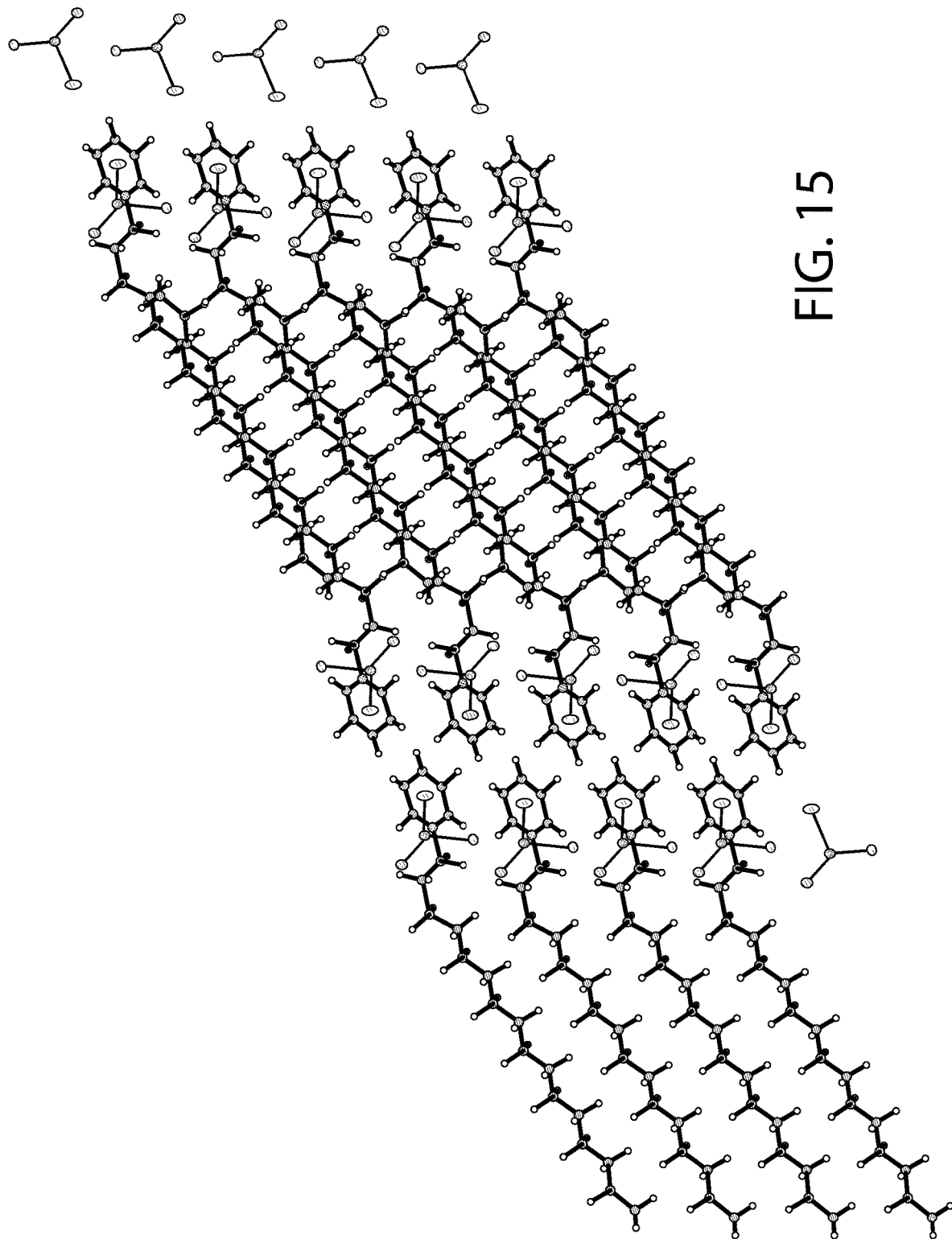
FIG. 15 illustrates packing of the structure illustrated in FIG. 14.

FIG. 14 illustrates an X-ray diffraction (SCXRD) analysis of a CPC-$SnCl_2$ complex according to an implementation. FIG. 15 illustrates packing of the structure illustrated in FIG. 14. The X-ray diffraction data was collected using a Bruker D8 Venture PHOTON 100 CMOS system equipped with a Cu Kα INCOATEC ImuS micro-focus source (λ=1.54178 Å). Data integration and reduction were performed using SaintPlus 6.01. Absorption correction was performed by multi-scan method implemented in SADABS. Space group was determined using XPREP implemented in APEX3. The structure was solved using SHELXT (direct methods) and was refined using SHELXL-2017 (full-matrix least-squares on F2) through OLEX2 interface program. All non-hydrogen atoms were refined anisotropically. Hydrogen atoms were placed in geometrically calculated positions and were included in the refinement process using riding model.

As illustrated in FIGS. 14-15, the solved crystal structure and packing arrangement for the CPC-$SnCl_2$ complex show that the molecules are arranged in a 1:1 ratio with a cetylpyridinium cation and $SnCl_3$ anion. The alkyl chains of CPC align with one another with the polar head groups facing in opposite directions for consecutive molecules. The pyridine rings are aligned in parallel in respect to one another. As a result of the packing arrangement (FIG. 15), there is a non-polar region consisting of the stacked alkyl chains and a polar region consisting of the cationic pyridine rings and $SnCl_3^-$ anions.

Accordingly, as illustrated in FIGS. 12-15, in some implementations, the CPC-SnCl$_2$ complex can be described as having a $[C_{21}H_{38}N][SnCl_3]$ structural formula. In addition, the crystallization analysis described above further evidence that the CPC-SnCl$_2$ complex is also not a mere mixture of CPC and SnCl$_2$, but involves a covalently or ionically-bound complex.

As described in the present disclosure, the inventors have created an oral care composition that includes an antibacterial agent including novel cetylpyridinium complexes, such as a CPC-ZnCl$_2$ complex or a CPC-SnCl$_2$ complex. In some implementations, the CPC-ZnCl$_2$ complex has a structural formula of $[(C_{21}H_{38}N)_2][ZnCl_4]$.

In some implementations, the cetylpyridinium complex, such as a CPC-ZnCl$_2$ complex, is the only antibacterial agent in the oral care composition. In other implementations, the cetylpyridinium complex, such as a CPC-ZnCl$_2$ complex, is part of a mixture of antibacterial agents in the oral care composition.

The oral care compositions may include an amount of cetylpyridinium complex sufficient to inhibit or retard the growth of bacteria in the oral cavity. In one implementation, the oral care composition may include from about 0.01 weight % to about 2.0 weight % CPC-ZnCl$_2$ complex, based on the total weight of the oral care composition. For example, the oral care composition may include from about 0.05 weight % to about 1.0 weight % CPC-ZnCl$_2$ complex, from about 0.10 weight % to about 0.75 weight % CPC-ZnCl$_2$ complex, or from about 0.25 weight % to about 0.50 weight % CPC-ZnCl$_2$ complex, based on the total weight of the oral care composition. In a preferred implementation, the oral care composition is a dentifrice and includes from about 0.01 weight % to about 1.0 weight % CPC-ZnCl$_2$ complex. In other implementations, the oral care composition is a mouthwash and includes about 0.1 weight % or less CPC-ZnCl$_2$ complex, based on the total weight of the oral care composition. For example, the oral care composition may include from about 0.001 weight % to about 0.1 weight % CPC-ZnCl$_2$ complex, from about 0.01 weight % to about 0.1 weight % CPC-ZnCl$_2$ complex, or from about 0.05 weight % to about 0.1 weight % CPC-ZnCl$_2$ complex. In other implementations, the oral care composition may include from about 0.01 weight % to about 2.0 weight % CPC-SnCl$_2$ complex, based on the total weight of the oral care composition.

In some implementations, the oral care composition may be a dentifrice and may include additional ingredients common to dentifrice-type oral care compositions, such as carriers, dispersants, whitening agents, flavoring agents, tartar control agents, surfactants, sweeteners, humectants, colorants, antibacterial agents, preservatives, dyes, and pigments.

All ingredients used in the compositions described herein should be orally acceptable. "Orally acceptable" means an ingredient which is present in the composition as described in an amount and form which does not render the composition unsafe, unpalatable, or otherwise unsuitable for use in the oral cavity. In addition, the additional ingredients should not substantially inhibit the efficacy of the antibacterial agent described herein.

The oral care composition may include one or more additional antibacterial agents or preservatives. In some implementations, the preservatives improve an antimicrobial characteristic of the oral care composition to improve storage life or prevent decay.

In certain implementations, the one or more antibacterial agents or preservatives include at least one of sodium benzoate, methyl paraben, ethyl paraben, zinc citrate, zinc oxide, triclosan, stannum salts, and combinations thereof.

The oral care composition may include an effective amount of antibacterial agents or preservatives. For example, the oral care composition may include an amount of antibacterial agents or preservatives effective to reduce spoilage of the oral care composition during storage or use.

In various implementations of the present disclosure, the oral care composition includes an orally acceptable carrier. As used herein, an "orally acceptable carrier" refers to a material or combination of materials that are safe for use in the oral care compositions of the present disclosure while retaining significant efficacy for the antibacterial agent(s). In certain implementations, the carrier is specifically selected to ensure that there is no substantially reduction in efficacy for the antibacterial agent(s). For example, the oral care composition may use water as the carrier. In certain implementations, the oral care composition includes 90 weight % or less, 70 weight % or less, or 50 weight % or less carrier, based on the total weight of the oral care composition.

In certain implementations, the oral care composition may include one or more humectants. In some implementations, the humectant is a mixture of humectants, such as glycerin and sorbitol, and a polyhydric alcohol, such as propylene glycol, butylene glycol, hexylene glycol, polyethylene glycol. In certain implementations, the oral care composition includes from 5 weight % to 40 weight % or from 10 weight % to 30 weight % humectant, based on a total weight of the oral care composition.

The oral care composition may include one or more whitening agent. As used herein, a "whitening agent" is a material that affects whitening of a tooth surface to which it is applied. For example, in some implementations, the whitening agent is an oxidizing agent. In its broadest sense, "oxidizing agent" is intended to include those compounds which may accept an electron from another molecule in the environment of the oral cavity without having a deleterious or unacceptably harmful effect on the oral cavity in normal and accepted use.

In some implementations, the whitening agent may include peroxides and hydroperoxides, such as hydrogen peroxide, peroxides of alkali and alkaline earth metals, organic peroxy compounds, peroxy acids, salts thereof, and mixtures thereof. The whitening agent may include peroxides of alkali and alkaline earth metals include lithium peroxide, potassium peroxide, sodium peroxide, magnesium peroxide, calcium peroxide, barium peroxide, and mixtures thereof. The whitening agent may include organic peroxy compounds include urea peroxide, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. The whitening agent may include peroxy acids and their salts include organic peroxy acids such as alkyl peroxy acids, and monoperoxyphthalate and mixtures thereof, as well as inorganic peroxy acid salts such as percarbonate, perphosphate, perborate and persilicate salts of alkali and alkaline earth metals such as lithium, potassium, sodium, magnesium, calcium and barium, and mixtures thereof. In some implementations a non-peroxide whitening agent may be provided. Whitening agents among those useful herein include non-peroxy compounds include chlorine dioxide, chlorites and hypochlorites. Non-peroxide whitening agents include chlorites and hypochlorites, including those of alkali and alkaline earth metals such as lithium, potassium, sodium, magnesium, calcium and barium. Non-peroxide whitening agents also include colorants, such as titanium dioxide and hydroxyapatite.

In some implementations, the oral care composition includes from about 0.01% to about 50% whitening agent based on a total weight of the oral care composition. For example, the oral care composition includes from about 0.05 weight % to about 40 weight % whitening agent. In one implementation, the oral care composition includes about 0.1 weight % whitening agent based on a total weight of the oral care composition.

In one implementation, the oral care composition includes one or more surfactants. In some implementations, the surfactants enhance stability of the composition, help clean the oral cavity surfaces through detergency, and provide foam upon agitation, e.g., during brushing with an oral care composition of the disclosure. Surfactants or surface active agents generally achieve increased whitening action by thoroughly dispersing the whitening agent throughout the oral cavity. In various implementations, suitable surfactants may function as a surface active agent, emulsifier, and/or foam modulator.

Any orally acceptable surfactant, most of which are anionic, nonionic, cationic, or amphoteric, may be used. A combination of surfactants may also be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium lauryl ether sulfate, ammonium lauryl sulfate, ammonium lauryl ether sulfate, sodium cocoyl monoglyceride sulfonate, sodium lauryl sarcosinate, sodium lauryl isoethionate, sodium laureth carboxylate, and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include, without limitation, derivatives of $C_{8-20}$ aliphatic secondary and tertiary amines having an anionic group such as carboxylate, sulfate, sulfonate, phosphate or phosphonate. A suitable example is cocoamidopropyl betaine.

In some implementations, the oral care composition includes from about 0.01% to about 20.0% surfactant based on a total weight of the oral care composition. For example, the oral care composition includes from about 1.0 weight % to about 10.0 weight % surfactant. In one implementation, the oral care composition includes about 2 weight % surfactant based on a total weight of the oral care composition. For example, the oral care composition may include about 2 weight % sodium lauryl sulfate.

In certain implementations, the oral care composition may include thickening agents or thickeners. Any orally acceptable thickening agent may be used, including without limitation carbomers, also known as carboxyvinyl polymers, carrageenans, also known as Irish moss and more particularly carrageenan (iota-carrageenan), high molecular weight polyethylene glycols (such as CARBOWAX™, available from The Dow Chemical Company), cellulosic polymers such as hydroxyethylcellulose, carboxymethylcellulose ("CMC") and salts thereof, e.g., CMC sodium, natural gums such as karaya, xanthan, gum arabic and tragacanth, colloidal magnesium aluminum silicate, and colloidal or fumed silica and mixtures of the same. The thickening agent may be a combination of one or more orally acceptable thickening agents.

In some implementations, the oral care composition includes from about 0.01% to about 30% thickening agent based on a total weight of the oral care composition. For example, the oral care composition includes from about 0.1 weight % to about 20 weight % thickening agent. In yet another example, the oral care composition includes from about 0.5 weight % to about 10 weight % thickening agent based on a total weight of the oral care composition. For example, the oral care composition may include about 3 weight % fumed silica.

In some implementations, the oral care composition includes an antioxidant. Acceptable antioxidants include BHA, BHT, vitamin A, vitamin C, carotenoids, vitamin E, flavonoids, polyphenols, ascorbic acid, herbal antioxidants, chlorophyll, melatonin and mixtures thereof. In some implementations, the oral care composition includes from about 0.001% to about 1% antioxidants based on a total weight of the oral care composition. In one implementation, the oral care composition includes about 0.03 weight % antioxidant by weight.

In certain implementations, the oral care composition includes one or more flavoring agents. Useful flavoring agents include any material or mixture of materials operable to enhance the taste of the oral care composition. Any orally acceptable natural or synthetic flavoring agent may be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavoring agents herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, x-irisone, propenyl guaiethol, thymol, linalool, benzaldehyde, cinnamaldehyde, N-ethyl-p-menthan-3-carboxamine, N, 2,3-trimethyl-2-isopropylbutanamide, 3-1-menthoxypropane-1,2-diol, cinnamaldehyde glycerol acetal (CGA), methone glycerol acetal (MGA) and mixtures thereof.

In some implementations, the oral care composition includes from about 0.01% to about 5% flavoring agents based on a total weight of the oral care composition. For example, the oral care composition includes from about 0.05 weight % to about 3 weight % flavoring agents. In yet another example, the oral care composition includes from about 0.1 weight % to about 3 weight %, from about 0.2 weight % to about 2.5 weight %, or about 1.5 weight % flavoring agents based on a total weight of the oral care composition. For example, the oral care composition may include about 1.5 weight % of dental cream flavor.

In some implementations, the oral care composition may also include one or more sweeteners. Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones and mixtures thereof. Some implementations may include one or more sweeteners. In some implementations, the oral care composition includes from about 0.005% to about 5% sweeteners based on a total weight of the oral care composition. In other implementations, the oral care composition includes from about 0.01% to about 1% sweeteners based on a total weight of the oral care composition. For example, the oral care composition may include about 0.5 weight % sodium saccharin and about 0.04 weight % sucralose.

In some implementations, the oral care composition may include colorants. Colorants, such as dyes or pigments, may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-DELTA-3,5-cyclohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants, if included, are present in very small quantities.

In some implementations, the oral care composition may also include one or more pH modifying agents. The pH modifying agents among those useful herein include acidifying agents to lower pH, basifying agents to raise pH and buffering agents to control pH within a desired range. For example, one or more compounds selected from acidifying, basifying and buffering agents may be included to provide a pH of 2 to 10, or in various implementations from about 2 to about 8, from about 3 to about 9, from about 4 to about 8, from about 5 to about 7, from about 6 to about 10, and from about 7 to about 9. Any orally acceptable pH modifying agent may be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range. In some implementations, the oral care composition includes from about 0.01% to about 10% pH modifier agents based on a total weight of the oral care composition. For example, the oral care composition may include about 0.9 weight % sodium acid pyrophosphate (SAPP) and about 2 weight % tetrasodium pyrophosphate (TSPP) as a pH modifier.

The oral care composition of the present disclosure may also include one or more additional active ingredients, which are operable for the prevention or treatment of a condition or disorder of hard or soft tissue of the oral cavity, the prevention or treatment of a physiological disorder or condition, or to provide a cosmetic benefit.

Some implementations of the present disclosure include a dental abrasive or combination of dental abrasive agents. As used herein, the term "abrasive" or "abrasive agent" also includes materials commonly referred to as "polishing agents." Any orally acceptable abrasive may be used, but typically, type, fineness (particle size) and amount of abrasive should be selected so that tooth enamel is not excessively abraded in normal use of the composition. Suitable abrasives include without limitation silica (in the form of silica gel, hydrated silica or precipitated silica), alumina, insoluble phosphates, calcium carbonate, resinous abrasives such as urea-formaldehyde condensation products and the like.

Among insoluble phosphates useful as abrasives are orthophosphates, polymetaphosphates and pyrophosphates. Illustrative examples are dicalcium orthophosphate dihydrate, calcium pyrophosphate, n-calcium pyrophosphate, tricalcium phosphate, calcium polymetaphosphate and insoluble sodium polymetaphosphate.

Average particle size of an abrasive, if present, is generally from about 0.1 to 100 about µm. For example, in one implementation, the particle size is from about 1 to about 80 µm or from about 5 to about 60 µm. In some implementations, one or more abrasives are present in an amount of from about 0.01% to about 70% by weight, based on the total weight of the oral care composition. In other implementations, the oral care composition includes from about 0.1 weight % to about 60 weight % abrasives. In some implementations, the abrasive is calcium pyrophosphate. In some implementations, the oral care composition includes from 0.01 weight % to about 70 weight % calcium pyrophosphate based on a total weight of the oral care composition. In another implementation, the oral care composition includes about 20 weight % calcium pyrophosphate.

In various implementations of the present disclosure, the oral care composition includes an anticalculus agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, and diphosphonates. In some implementations, the anticalculus agent is present in an amount of from about 0.01% to about 30% weight based on the total weight of the oral care composition. In some implementations, the oral care composition includes a mixture of anticalculus agents. In some implementations, tetrasodium pyrophosphate (TSPP) and sodium tripolyphosphate (STPP) are used as the anticalculus agents. In some implementations, the anticalculus agent includes from 0.1% to 10 weight % TSPP, or about 2 weight % TSPP.

The oral care compositions of the present disclosure may also include a synthetic anionic polymeric polycarboxylate. The synthetic anionic polymeric polycarboxylate can act as a stabilizer for the polyphosphate anti-calculus agent and may help to block access of painful or pain-causing materials, such as sugars, to the tooth nerves.

In some implementations, the oral care composition optionally includes a source of fluoride ions. In some implementations, the source of fluoride ions is selected from: fluoride, monofluorophosphate (MFP), and fluorosilicate salts. In some implementations, one or more fluoride ion-releasing compounds are optionally present in an amount providing a total of 100 to 20,000 ppm, 200 to 5,000 ppm, or 500 to 2,500 ppm, fluoride ions. If present, in some implementations, the amount of fluoride source in the oral care composition ranges from about 0.01% to about 10% by weight, based on the total weight of the oral care composition, typically about 0.5% to about 1.5 weight %. For example, in one implementation, the oral care composition may include about 0.76 weight % MFP.

The compositions also may include a stannous ion or a stannous ion source to mitigate calcium loss. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. In some implementations, one or more stannous ion sources are included in the oral care composition. For example, the oral care composition may include from about 0.01% to about 10% stannous ion source by weight, based on the total weight of the oral care composition. In one implementation, the oral care composition includes from about 0.1 weight % to about 7 weight % stannous ion source or from about 0.2 weight % to about 5 weight % stannous ion source.

EXAMPLES

Aspects of the present disclosure may be further understood by referring to the following examples. The examples are illustrative, and are not intended to be limiting implementations thereof.

Example 1

Table 1 describes the results of an assay evaluating the antibacterial efficacy of an exemplary CPC-$ZnCl_2$ complex of the present invention, in the presence of an anionic surfactant. In particular, the antibacterial efficacy of a CPC-$ZnCl_2$ complex was compared to $ZnCl_2$ and CPC individually, in the presence of SLS, as follows: human saliva was collected and diluted three times with deionized water, centrifuged, and decanted to yield a translucent solution of oral bacteria. 10 mg (+/− 0.7 mg) of the antibacterial ingredient (CPC-$ZnCl_2$ complex, CPC, and $ZnCl_2$) was combined with 20 mg (+/− 0.9 mg) of a 30 weight % SLS aqueous solution and 5 ml of the prepared oral bacteria solution. A negative control was also prepared adding 20 mg (+/− 0.9 mg) of the 30 weight % SLS aqueous solution and 5 ml of the prepared oral bacteria solution to deionized water instead of the antibacterial ingredient. The samples were then placed in a 37° C. oven and shaken at 100 RPM for 30 minutes. 200 µL of Alamar Blue dye was then added to each sample and placed back in the 37° C. oven and shaken at 100 RPM. The samples were then monitored every 30 minutes, with the results 1 hour after addition of the dye recorded in Table 1. In the Alamar Blue assay, a color change from blue to red indicates the presence of live bacteria.

TABLE 1

| Active | Color of Solution |
| --- | --- |
| CPC—$ZnCl_2$ complex | Blue |
| CPC | Pink |
| $ZnCl_2$ | Purple |
| Control | Pink |

As illustrated in Table 1, both the Control and the CPC sample turned pink, indicating the presence of live bacteria. The $ZnCl_2$ sample turned purple, also indicating the presence of live bacteria. However, the CPC-$ZnCl_2$ complex sample remained blue, indicating the absence of live bacteria. The results of Table 1 demonstrate that the cationic antibacterial-metal salt complexes of the present invention provide antimicrobial efficacy, even in the presence of an anionic surfactant. These results are truly surprising given the anticipated interaction between cationic antibacterial agents and anionic surfactants, which renders cationic antibacterial agents largely ineffective. As such, these results demonstrate a breakthrough in formulating cationic antibacterial agents with anionic surfactants, which may significantly expand the use of efficacious and inexpensive cationic antibacterial agents in oral care. The data described Table 1 also illustrates that the CPC-$ZnCl_2$ complex is not merely a mixture of CPC and $ZnCl_2$; rather, it is a distinct chemical entity. Without being bound by theory, the results observed herein suggest the presence of a covalently or ionically-bound complex.

Example 2

Table 2 describes a dentifrice according to some implementations of the present disclosure. Table 3 illustrates a mouthwash according to some implementations of the present disclosure.

TABLE 2

| Ingredients | Wt. % |
| --- | --- |
| CPC—$ZnCl_2$ | 0.1-2.0 |
| Sorbitol | 35 |
| Carrageenan | 0.2 |
| Silica, dicalcium orthophosphate dehydrate | 20 |
| Anionic surfactant (e.g. SLS) | 1.5 |
| Fluoride ion source | 0.24 |
| Tetra sodium pyrophosphate | 2 |
| Flavor | 0.5-2.0 |
| Water and minors | q.s |

TABLE 3

| Ingredients | Wt. % |
| --- | --- |
| CPC—$ZnCl_2$ complex | 0.01-2.0 |
| Anionic surfactant (e.g. SLS) | 1.5 |
| Glycerin | 23 |
| Propylene glycol | 16.07 |
| Sorbitol | 23 |
| Poloxamer | 0.5 |
| Flavor | 0.1 |
| Sodium saccharin | 0.05 |
| Water and minors | q.s |

The exemplary compositions described in Tables 2 and 3 (above) may be prepared according to conventional methods known to those skilled in the art. In particular, the exemplary compositions are prepared to ensure that the CPC-$ZnCl_2$ complex provides effective antibacterial activity in the presence of an anionic surfactant (e.g. SLS).

Example 3

Separate vials containing twenty-five percent (25%) solutions of CPC and seventy-five percent (75%) solutions of $ZnCl_2$ are prepared. These solutions are then diluted 10×, 100×, and 1000×, and kept in separate vials. Thereafter, each of the diluted CPC and $ZnCl_2$ solutions are combined at a Zn:CPC molar ratio of 2:1 (e.g. the 10× diluted solution of CPC is combined with the 10× diluted solution of $ZnCl_2$). A precipitate was only observed at concentrations significantly higher than those found in oral care compositions. These results demonstrate that the complexes of the present invention do not spontaneously form in compositions comprising typical concentrations of CPC and $ZnCl_2$. While the examples above describe a molar ratio, the present disclosure is not limited thereto, and other molar ratios may be used to create the complexes of the present disclosure. For example, the CPC and $ZnCl_2$ solutions may be combined at other molar ratios to create the CPC-$ZnCl_2$ complex. In one implementation, the Zn:CPC molar ratio may be 0.5-2.0:1. In another implementation, the Zn:CPC molar ratio may be 0.1-4.0:1.

The present disclosure has been described with reference to exemplary implementations. Although a few implementations have been shown and described, it will be appreciated by those skilled in the art that changes may be made in these implementations without departing from the principles and spirit of preceding detailed description. It is intended that the present disclosure be construed as including all such modifications and alterations insofar as they come within the scope of the appended claims or the equivalents thereof.

What is claimed is:

1. An oral care composition, comprising:
   a complex comprising a cationic antibacterial agent and a metal salt;
   a surfactant;
   a cosmetically acceptable carrier, wherein the metal salt is a stannous salt and the cationic antibacterial agent is cetylpyridinium chloride (CPC), and wherein the complex has a structural formula of $[C_{21}H_{38}N][SnCl_3]$; and;
   an oral care ingredient selected from: a thickening agent; an abrasive; a film; a whitening agent; a flavorant; a colorant; a pH modifying agent; and a sensitivity reducing agent.

2. The oral care composition according to claim 1, wherein the surfactant is an anionic surfactant selected from: sodium lauryl sulfate, sodium lauryl ether sulfate, ammonium lauryl sulfate, ammonium lauryl ether sulfate, sodium cocoyl monoglyceride sulfonate, sodium lauryl sarcosinate, sodium lauryl isoethionate, sodium laureth carboxylate, sodium dodecyl benzenesulfonate; and combinations of two or more thereof.

3. The oral care composition according to claim 1, comprising from about 0.01 wt. % to about 1.0 wt. % of said complex.

4. The oral care composition according to claim 1, comprising from about 0.10 wt. % to about 0.75 wt. % of said complex.

5. The oral care composition according to claim 1, wherein the oral care composition is in a form selected from a paste; a gel; a mouthwash or mouthrinse; and a prophy.

6. A method of treating, inhibiting, preventing, or ameliorating a symptom associated with a disease or condition of the oral cavity in a subject in need thereof, comprising: administering the complex according to claim 1, to an oral cavity surface of said subject.

7. The method according to claim 6, wherein the disease or condition of the oral cavity is selected from: erosion; malodor; excessive plaque; gingivitis; biofilm build-up; tooth decay; caries; and dentinal hypersensitivity.

* * * * *